United States Patent [19]

Wong et al.

[11] Patent Number: 5,106,750
[45] Date of Patent: Apr. 21, 1992

[54] ENANTIO- AND REGIOSELECTIVE SYNTHESIS OF ORGANIC COMPOUNDS USING ENOL ESTERS AS IRREVERSIBLE TRANSACYLATION REAGENTS

[75] Inventors: Chi-Huey Wong; Yi-Fong Wang, both of College Station; William J. Hennen, Bryan, all of Tex.; Kevin A. Babiak, Evanston, Ill.; John H. Dygos, Northbrook, Ill.; John S. Ng, Chicago, Ill.

[73] Assignee: G. D. Searle & Co., Chicago, Ill.

[21] Appl. No.: 396,723

[22] Filed: Aug. 24, 1989

Related U.S. Application Data

[63] Continuation-in-part of Ser. No. 238,358, Aug. 30, 1988, abandoned.

[51] Int. Cl.$^5$ ............................................. C12P 41/00
[52] U.S. Cl. .................................. 435/280; 435/134; 435/135
[58] Field of Search .................... 435/280, 135, 134

[56] References Cited

U.S. PATENT DOCUMENTS

| | | | |
|---|---|---|---|
| 4,511,655 | 4/1985 | Minai et al. | 435/280 |
| 4,607,013 | 8/1986 | Mitsuda et al. | 435/280 |
| 4,916,074 | 4/1990 | Yoshida et al. | 435/280 |
| 4,933,290 | 6/1990 | Cesti et al. | 435/280 |
| 4,957,867 | 9/1990 | Minai et al. | 435/135 |

FOREIGN PATENT DOCUMENTS

| | | | |
|---|---|---|---|
| 247620 | 12/1987 | European Pat. Off. | 435/135 |
| 264707 | 2/1989 | German Democratic Rep. | 435/135 |

OTHER PUBLICATIONS

Therisod et al, Facile Enzymatic Preparation of Monoacylated etc., J. Am. Chem. Soc., 108, 5638–5640, Apr. 1986.
Riva et al, Protease-Catalyzed Regioselective etc., J. Am. Chem. Soc., 110 (2), 584–589, Jan. 1988.
Degueil-Castaing, M. Enzymatic Reactions in Organic Synthesis: etc., Tet. Let., 28 (9), 953–954, Sep. 1987.
Sweers et al, Enzyme-Catalyzed Regioselective Deacylation of etc., J. Am. Chem. Soc., 108, 6421–6422, May 1986.
Wang et al, Lipase Catalyzed Irreversible etc., J. Org. Chem., 53, 3127–3129, Feb. 1988.
Gil et al, Lipase-Catalyzed Ester Formation in Organic etc., Tet. Let., 28 (15), 1647–1648, 1987.
Ramos Tombo et al, Synthesis of Both Enantiomeric Forms of etc., Tet. Let., 27 (47), 5707–5710, Aug. 1986.
J. Bryan Jones, Enzymes in Organic Synthesis, Tetrahedron, 42 (13), 3351–3403, 1986.
Mitsunobu et al, Preparation of Carboxylic Esters and etc., Bull Chem. Soc. Japan, 44, 3427–3430, May 1971.
Mitsunobu et al, Stereospecific and Stereoselective Reactions. etc., JACS, 94 (2), 679–680, Jan. 1972.
Mitsunobu et al, Preparation of Esters of Carboxylic and etc., Bull Chem. Soc. Japan, 40 (10), 2380–2382, Feb. 1967.
Whitesides et al, Enzymes as Catalysts in Synthetic Organic etc., Ange. Chem., 24 (8), 617–718, Aug. 1985.
Rothman et al, Acid-Catalyzed Interchange Reactions of etc., J. Org. Chem., 27, 2123–3127, Sep. 1962.
Butt et al, Opportunities for Using Enzymes in Organic etc., Chem. in Britian, 127–134, Feb. 1987.
Akiyama et al, Enzymes in Organic Synthesis, Chem. in Britian, 645–654, Jul. 1987.
Klibanov, A., Enzymes that Work in Organic Solvents, Chemtech, 354–359, Jun. 1986.
Chen, C–H et al, Quantitative Analyses of Biochemical Kinetic etc., J. Am. Chem. Soc., 109 (9), 2812–2817, 1987.
Zhi-Wei et al, Enzymatic Synthesis of Macrocyclic Lactones, J. Am. Chem. Soc., 110 (6), 1999–2001, Mar. 1988.
Yokozeki et al, Application of Immobilized Lipase to etc., Eur. J. App. Microbiol. Biotech., 14, 1–5, 1982.
Belan et al, Use of Biological Systems for the Preparation etc., J. Org. Chem., 52 (2), 256–260, Feb. 1987.
Swern et al, Vinyl Laurate and other Vinyl Esters, Org. Synth., IV, 977–980, 1963.
Wang, Y–F et al, Bifunctional Chiral Synthons via Biochemical etc., J. Am. Chem. Soc., 106, 3695–3696, 1984.
Wang Y–F, Bifunctional Chiral Synthons via Biochemical etc., Tet. Let., 25 (44), 4999–5002, Jan. 1984.
Suemune et al, Enzymatic Synthesis of etc., Chem. Phar. Bull., 34 (8), 3440–3444, Feb. 1986.
Hirth et al, Synthesis of Glyceryletherphosphatides (Title etc. Helv. Chim. Acta, 65 (3), 1059–1084, 1982.
Stork et al, Stereospecific Reductive Methylation via a etc., J. Am. Chem. Soc., 108 (21), 6826–6828, Apr. 1986.
Mori et al, Synthesis and Bioactivity of Optically Active etc., Tetrahedron, 43 (10), 2249–2254, Oct. 1987.
Durrwachter et al, Fructose 1,6-Diphosphate Aldolase Catalyzed etc., J. Org. Chem., 53, 1018, Mar. 1988.
Stokes et al, Enzyme Reactions in Apolar Solvents: The etc., Tet. Let., 28 (19), 2091–2084, Dec. 1987.
Gokel et al, The Retentive Nucleophilic Displacements of etc., J. Org. Chem., 37 (20), 3052–3058, Mar. 1972.
Langrand et al, Lipase Catalyzed Reactions and Strategy for etc., Tet. Let., 27 (1), 29–32, 1986.
Cambou et al, Preparative Production of Optically Active etc., J. Am. Chem. Soc., 106 (9), 2687–2692, Apr. 1984.

*Primary Examiner*—Carolyn Elmore
*Attorney, Agent, or Firm*—Cynthia S. Kovacevic; P. D. Matukaitis; R. A. Williams

[57] ABSTRACT

A process for irreversible regio- and stereoselective enzyme catalyzed acylation of alcohols using enol esters as acylating reagents is disclosed. The present invention permits the selective modification of hydroxyl group(s) of chiral and meso alcohols, including sugars, organometallics, and glycosides. The enol freed upon transesterification rapidly tautomerizes to the corresponding volatile aldehyde or ketone thereby preventing the reverse reaction from occurring.

18 Claims, No Drawings

ENANTIO- AND REGIOSELECTIVE SYNTHESIS OF ORGANIC COMPOUNDS USING ENOL ESTERS AS IRREVERSIBLE TRANSACYLATION REAGENTS

This is a continuation-in-part of application Ser. No. 07/238,358, filed Aug. 30, 1988, abandoned.

BACKGROUND OF THE INVENTION

The present invention relates to enantio- and regioselective synthesis of esters of alcohols, sugars, organometallics and glycosides and to their preparation using enzyme mediated transesterification. More particularly, the present invention relates to enzyme catalyzed irreversible transesterification using enol esters as transacylation reagents.

Hydrolytic enzymes such as lipases, esterases, and proteases have been used extensively as catalysts in enantioselective syntheses. Whitesides, G. M., Wong, C-H. *Angew. Chem. Int. Ed. Engl.* 24 (1985) 617; Jones, J. B. *Tetrahedron* 42 (1986) 3351; Roberts, S. M. *Chem. Br.* (1987) 127; Akiyama, A., Bednarski, M., Kim, M. J., Simon, E. S., Waldmann, H. I., Whitesides, G. M. Ibid. (1987) 645. Because of their relatively high stability in organic media, many hydrolytic enzymes also can be used in organic solvents for certain types of transformation which are difficult to do in water. The most common reactions are esterase and lipase-catalyzed stereoselective esterifications and transesterifications. Klibanov, A. M. *CHEMTECH* (1986) 354-9; Klibanov, A. M., Cambou, B. *J. Am. Chem. Soc.* 106 (1984) 2687-92. Chen, C-S., Wu, S-H., Girdaukas, G., Sih, C. J. *J. Am. Chem. Soc.* 109 (1987) 2812-17; Guo, Z. W., Sih, C. J. Ibid. 110 (1988) 1999-2001; Gil, G., Ferre, E., Meou, A., Petit, J. L., Triantaphylides, C. *Tetrahedron Lett.*28 (1987) 1647; Yokozeki, K., Yamanaka, S., Takinami, K., Hirose, Y., Tanaka, A., Sonomoto, K., Fukui, S. *Eur. J. Appl. Microbiol. Biotechnicol* 14 (1982) 1; Tambo, G. M. R., Schar, H-P., Busquets, X. F., Ghisalba, O. *Tetrahedron Lett.* 27 (1986) 5705-10; Belan, A., Bolte, J., Fauve, A., Gourey, J. G., Veschambre, H. *J. Org. Chem.* 52, 256-60. Langrand, G., Baratti, J., Buono, G., Triantaphylides, C. *Tetrahedron Lett.* 27 (1986) 29-32.

One disadvantage of enzyme catalyzed hydrolytic reactions is that they are very slow compared to simple hydrolyses. Langrand, G., Baratti, J., Buono, G., Triantaphylides, C. *Tetrahedron Lett.* 27 (1986) 29-32. In addition, the products produced by enzymatic hydrolyses very often have to be separated from other by-products (particularly alcohol generated from the acylating reagent). Due to the reversible nature of these reactions, and due to the same stereoselectivity of the enzyme catalysis in both directions, the optical purity of the product obtained decreases as the reverse reaction proceeds. This situation is illustrated in FIG. 1 where a racemic alcohol is to be resolved via an enzymatic esterification (R"=H) or transesterification.

Figure 1:
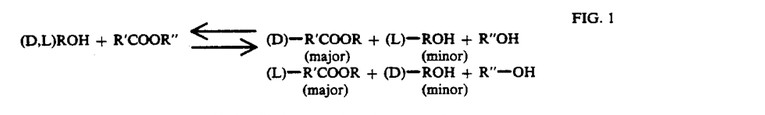

As shown in FIG. 1, if the D-isomer is a better substrate than the L-isomer for the enzyme, accumulation of the D-ester and the unreactive L-alcohol will be observed. In the reverse reaction, however, the D-ester is a better substrate and will be converted to the D-alcohol. The enantiomeric excess of both the D-ester and the L-alcohol therefore will decrease progressively as the extent of the reverse reaction increases. This reverse reaction problem clearly has been illustrated in the kinetic resolution of menthol, Chen, C-S., Wu, S-H., Girdaukas, G., Sih, C. J. *J. Am. Chem. Soc.* 109 (1987) 2812-17; Guo, Z. W., Sih, C. J. Ibid. 110 (1988) 1999-2001, and can be seen in the enantioselective esterification or transesterification of meso compounds.

SUMMARY OF THE INVENTION

The method of the present invention blocks the progress of the reverse reaction. The present invention is a process for irreversible regio- and stereoselective enzyme catalyzed acylation of alcohols using enol esters as acylating reagents. The present invention permits the selective modification of hydroxyl group(s) of chiral and meso alcohols, including sugars, organometallics and glycosides. The enol freed upon transesterification rapidly tautomerizes to the corresponding volatile aldehyde or ketone thereby preventing the reverse reaction from occuring.

DETAILED DESCRIPTION OF THE INVENTION

Nuclear magnetic resonance (NMR) spectra were recorded on a Varian XL-200E spectrometer. All chemical shifts were reported in ppm using tetramethylsilane as an internal standard unless otherwise indicated. Rotations were determined on a Perkin Elmer 240 polarimeter. Gas chromatographic (GC) analyses were performed on a Hewlett-Packard 5890 instrument with a 20-m DB-5 megabore column. The lipases from *PSEUDOMONAS* species (PSL, Type XIII), porcine pancreas (PPL, Type II), and *CANDIDA CYLINDRACEA* (CCL, Type VII) were obtained from Sigma Chemical Company. Cholesterol esterase was obtained from Amano Paramaceutical Company. Vinyl Acetate ($5 Kg, bp 72° C.) and isopropenyl acetate ($25 /Kg, bp 90° C.) were from Aldrich Chemical Co. Vinyl propionate ($25/25 g, bp 93°-94° C.) was from Pfaltz and Bauer, Inc. Some experimental protocols are described in Tables 1, 3 and 4.

The procedure for preparation of isopropenyl valerate (Ib of FIG. 2) was similar to that reported for the preparation of other isopropenyl esters, with some modifications. Rothman, E. S., Serota, S., Perlstein, T., Swern, D. *J. Org. Chem.* 27 (1962) 3123-27. To a 250 mL round bottom flask was added 10 mL of valeric acid (91.9 mmol) which had been freshly distilled, and 20 mL of valeric anhydride. Then, 200 mL of freshly distilled isopropenyl acetate was added followed by 2 drops of concentrated sulfuric acid. The mixture then was heated to reflux under an atmosphere of argon for 10 h, after which time all of the valeric acid had been consumed as evidenced by capillary GC. The reaction mixture was allowed to cool to room temperature and 0.5 g of sodium bicarbonate was added to quench the

FIG. 1 acid catalyst. The isopropenyl acetate then was removed by evaporation under reduced pressure. The orange liquid remaining was poured into 300 mL of 0° C. saturated sodium bicarbonate which was overlayed with 100 mL of diethyl ether. The mixture was stirred vigorously and the ether layer was analyzed by GC for the disapperance of the mixed valeric acetic anhydride. After all of the anhydride was consumed (6 h) the ether layer was separated and the aqueous layer was washed with 100 mL of ether. The combined ether layers were washed with 5×25 ml portions of saturated sodium bicarbonate to remove the valeric acid. The ether layer then was washed with saturated brine (30 mL) and the ether was then dried over sodium sulfate. The ether was removed under reduced pressure and the isopropenyl ester was purified by vacuum distillation (bp=50-52° C., 8 mm Hg). 7.85 g of a clear colorless liquid (lb) was obtained (60.1% yield). $^1$H-NMR (CDCl$_3$) 4.65 (m, 2H), 2.35 (t,2H) 1.90 (s, 3H), 1.65 (m, 2H), 1.35 (m, 2H), 0.90 (s, 3H). $^{13}$C-NMR 171.89, 153.00, 101.87, 34.02, 26.92, 22.16, 19.52, 13.16. In a similar manner isopropenyl butyrate was prepared from butyric acid in 54% yield. 3.68 g of isopropenyl butyrate were prepared from 4.85 mL of butyric acid and 10 mL of butyric anhydride. $^1$H-NMR 4.60 (m, 2H), 2.30 (t, 2H), 1.85 (s, 3H), 1.60 (m, 2H), 0.90 (t,3H).

Figure 2:
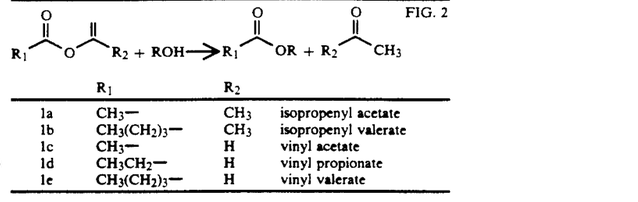

The method of Swern and Jordan was used to prepare vinyl valerate (le of FIG. 2). Swern, D., Jordan, E. F. *Organic Synthesis*, Coll. Vol. IV (1963) 977–80, incorporated herein by reference. Freshly distilled valeric acid (40 ml, 0.37 mol) and vinyl acetate (300 mL) were placed in a 3-necked 500 mL round bottomed flask fitted with a reflux condenser, a gas inlet tube and a thermometer. The solution was stirred under argon and mercuric acetate (1.2 g, 0.37 mmol) was added. The reaction mixture was stirred under argon for 30 min, after which time 10 drops of 100% sulfuric acid was added. The solution was heated to reflux for 6 h and then was allowed to cool to room temperature. Sodium acetate (1.0 g) was added to quench the acid catalyst. The excess vinyl acetate was removed by distillation under argon. The product (vinyl valerate) le was isolated by distillation (bp=135°-145° C.) as a clear colorless liquid (29.4 g, 62% yield). $^1$H-NMR 7.24 (m, 1H), 4.80 (m, 1H), 4.48 (m, 1H), 2.32 (t, 2H), 1.60 (m, 2H), 1.30 (m, 2H), 0.85 (t, 3H). $^{13}$C-NMR 170.69. 141.11, 97.22, 33.54, 26.57, 22.10, 13.57.

Any chiral or meso alcohol having no excessive steric hindrance can be used in the present method. Structures 15 and 16 of Table 2 represent compounds wherein excessive steric hindrance is present.

LIPASE-CATALYZED REACTIONS

A number of lipase-catalyzed irreversible transesterifications using enol esters as acylating reagents were performed in a manner outlined generally in FIG. 2.

FIG. 2

$$R_1 \overset{O}{\underset{}{\|}} O \overset{O}{\underset{}{\|}} R_2 + ROH \longrightarrow R_1 \overset{O}{\underset{}{\|}} OR + R_2 \overset{O}{\underset{}{\|}} CH_3$$

| | R$_1$ | R$_2$ | |
|---|---|---|---|
| la | CH$_3$— | CH$_3$ | isopropenyl acetate |
| lb | CH$_3$(CH$_2$)$_3$— | CH$_3$ | isopropenyl valerate |
| lc | CH$_3$— | H | vinyl acetate |
| ld | CH$_3$CH$_2$— | H | vinyl propionate |
| le | CH$_3$(CH$_2$)$_3$— | H | vinyl valerate |

The reactions produced optically active esters from several alcohols including those from glycerol and serinol derivatives, organometallics, nucleoside derivatives, sugars, and other chiral and racemic alcohols. The results are capsulized in Table 1.

TABLE 1

Lipase-catalyzed transesterifications with enol esters as acylating agents.

| Entry | Substrate | Enz | enol ester | % conversion | % ee alcohol (Config.) | % ee ester (Config.) |
|---|---|---|---|---|---|---|
| 1 | 2 | PSL | la | 72 | — | 96 (S) |
| 2 | 5 | PPL | le | 60 | — | 97 (R) |
| 3 | 8a | PSL | la | 32 | 29 (S) | 67 (R) |
| 4 | 8b[a] | PSL | H$_2$O | 50 | 92 (R) | — |
| 5 | 8a | PSL | lb | 25 | 21 (S) | 64 (R) |
| 6 | 8a | ChE | la | 33 | 22 (S) | 54 (R) |
| 7 | 8a | CCL | la | 21 | 14 (S) | 50 (R) |
| 8 | 9a | PPL | ld | 43 | — | 54 (S) |
| 9 | 9a | PPL | le | 45 | — | 39 (S) |
| 10 | 9a | PSL | ld | 50 | — | 18 (S) |
| 11 | 10a | PPL | ld | 40 | — | 33 (S) |
| 12 | 10a | PPL | lc | 40 | — | 42 (S) |
| 13 | 10b[a] | PPL | H$_2$O | 30 | 82 (S) | — |
| 14 | 10a | PPL | lc | 80 | 65 (R) | — |
| 15 | 10a | PPL | le | 40 | — | 30 (S) |
| 16 | 10a | ChE | la | 31 | 5 (R) | 10 (S) |
| 17 | 11a | PSL | lc | 30 | — | 70 (R) |
| 18 | 11b[a] | PSL | H$_2$O | 60 | 94 (R) | — |
| 19 | 12a | CCL | le | 30 | — | 37 (R) |
| 20 | 13a | PPL | lc | 37 | 56 (S) | 98 (R) |
| 21 | 13a | PPL | lc | 58 | >98 (S) | 71 (R) |
| 22 | 14a | PPL | lc | 27 | 37 (S) | 98 (R) |
| 23 | 14a | PPL | lc | 62 | >98 (S) | 61 (R) |
| 24 | 15 | CCL | lc | — | — | — |
| 25 | 16 | CCL | lc | — | — | — |
| 26 | 17a | PPL | ld | 40 | — | 84 (R) |
| 27 | 17a | PPL | ld | 40 | 60 | 84 (S) | — |

[a]The obtained optically active ester was used as substrate in hydrolysis in 0.1M phosphate buffer (pH 7) at 28° C. The pH was controlled at 7.0 during the reaction by addition of 1N NaOH. Monitoring of the reaction progress and isolation of the products were the same as that in transesterification reactions.

Figure 3:
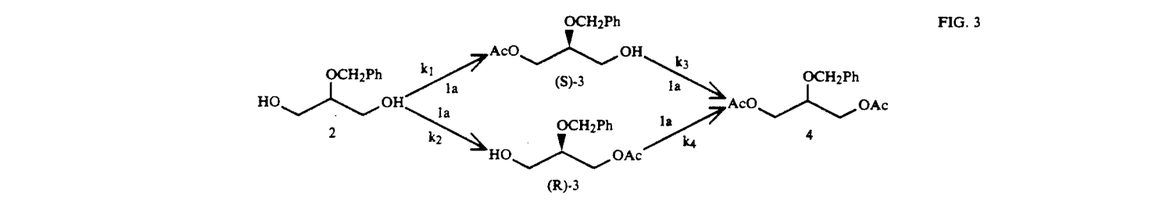
Figure 4:
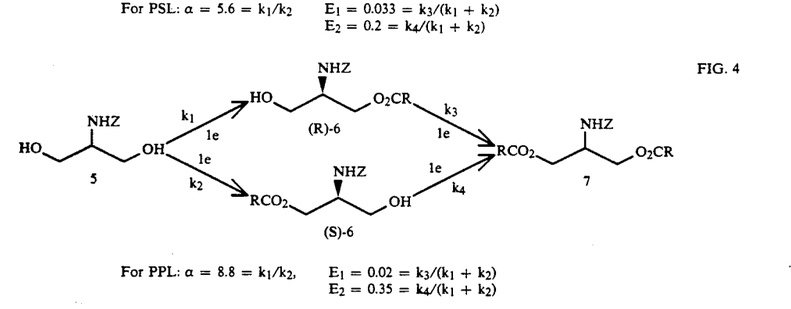

The reaction schemes for enantioselective acylation of 2-O-benzylglycerol (2) and N-carbobenzoxy serinol (5) are shown in FIGS. 3 and 4, respectively. The calculated kinetic parameters $\alpha$ and E are also listed.

FIG. 3

For PSL: $\alpha = 5.6 = k_1/k_2$  $E_1 = 0.033 = k_3/(k_1 + k_2)$
$E_2 = 0.2 = k_4/(k_1 + k_2)$

FIG. 4

For PPL: $\alpha = 8.8 = k_1/k_2$, $E_1 = 0.02 = k_3/(k_1 + k_2)$
$E_2 = 0.35 = k_4/(k_1 + k_2)$ Table 2 diagrams the starting materials and products formed from the reactions listed in Table 1, entries 3–27.

TABLE 2

17a R = H
17b R = propionyl

The general procedure used in the following lipase-catalyzed transesterifications was as follows:

The alcohol substrate and an excess of enol ester were dissolved in an organic solvent, such as pyridine or a less polar solvent. After a catalytic amount of enzyme was added, the suspension was stirred at 28° C. and the reaction was monitored by GC for conversion. Once the required extent of conversion was reached, the enzyme was filtered off and the solvent was removed by evaporation in a vacuum. The ester product and the unreacted alcohol were separated by chromatography on a silica gel column.

Some of the esters (e.g., acyl sugars) that were prepared can be obtained only in nearly anhydrous solvents due to thermodynamic reasons, or because of the lack of appropriate esterases to use in obtaining such esters via hydrolysis (e.g., (S)-3 in FIG. 3 and (R)-6 in FIG. 4). For example, in the kinetic resolution of ferrocenylethanol, the (R)-propionate ester obtained in toluene is stable towards solvolysis, while in ethanol or water, the ester decomposes to ferrocenylethylether or ferrocenylethanol.

TRANSESTERIFICATION OF SYMMETRICALLY PROCHIRAL DIOLS

EXAMPLE 1—PSL-catalyzed transesterification of 2-0-benzylglycerol (2 of FIG. 3) with isopropenyl acetate (1a of FIG. 2)

Chiral 3-0-acetyl-2-0-benzylglycerol ((R)- or (S)-3 of FIG. 3), and 3-0-acetyl-2-N-benzyloxycarbonyl serinol ((R) or (S)-6 of FIG. 5), are considered to be useful building blocks for the preparation of enantiomerically pure, biologically active molecules such as phospholipids, PAF (platelet-activating factor), phospholipase A2 inhibitors, sphingoglycolipids and many others. To prepare these chiral synthons, the prochiral diols, 2-0-benzylglycerol (2 of FIG. 3) and 2-N-benzyloxycarbonyl (Z) serinol (5 of FIG. 4) were chosen as substrates, respectively.

(a) A solution of 2-0-benzylglycerol (2 of FIG. 3) (300 mg, 1.65 mmol) and isopropenyl acetate (1a of FIG. 2) (0.73 mL, 6.6 mmol) in 4 mL of chloroform was mixed with 10 mg of PSL. After 27 h, the amounts of diacetate, monoacetate and diol were quantitatively determined to be 43:57:0 by GC analysis. The reaction was terminated and worked up as described in the general procedure. The products were separated by column chromatography (ethyl acetate:n-hexane-1:3) on silica gel to give 196 mg (53%) of monacetate ((S)-3 in FIG. 3), $[\alpha]^{23}_D$ −20.1 (c 1, CHCl$_3$), and 175 mg of diacetate (4 in FIG. 3). Monoacetate (S)-3: $^1$H-NMR 2.08 (3H, s), 3.60–3.78 (3H, m), 4.23 (2H, d, J=4.8 Hz), 4.61 (1H, d, J=11.8 Hz), 4.72 (1H, d, J=11.8 Hz), 7.35 (5H, s). Diacetate 4 in FIG. 3: $^1$H-NMR 2.06 (6H, s), 3.81 (1H, tt, J=5.2 Hz), 4.15 (2H, dd, J=5.2 Hz and 11.8 Hz), 4.25 (2H, dd, J=5.2 Hz and 11.8 Hz), 4.66 (2H, s), 7.34 (5H, s). The optical purity of monoacetate (15 mg) was determined to be 96% by $^1$H-NMR spectroscopy in the presence of Eu(hfc)$_3$ (30 mg). The relative intensities of the acetoxy group at 3.05 (major) and 2.90 (minor) were used for ee determination.

(b) A solution of 2-0-benzylglycerol (2 of FIG. 3) (3 mmol) and isopropenyl acetate (1a of FIG. 2) (12 mmol) in 6 mL of chloroform was mixed with 12 mg of the lipase from Pseudomonas (PSL) species at 28° C. with stirring. After 24 h, the amounts of diacetate, monoacetate and diol were quantitatively determined to be 10.0:82.6:7.4. The products were separated by column chromatography on silica gel to afford 538 mg (80%) of monoacetate ((S)-3 of FIG. 3), the optical purity of which was determined to be 75.5% by $^1$H-NMR spectroscopy in the presence of tris (3-(heptafluoropropyl-hydroxymethylene)-(+)-camphorato]europium (III) derivative (Eu(hfc)$_3$). The monoacetates produced in the transesterification reaction were expected to undergo further acetylation to yield the diacetate (4 of FIG. 3) and the enzyme was expected to show the same stereochemical preference in the second step (i.e. $k_4 > k_3$) as in the hydrolysis of meso diacetate compounds, so that the optical purity of monoacetate (S)-3 could be enhanced by increasing the conversion. Wang, Y. F., Chen, C. S., Girdaukas, G., Sih, C. J. *J. Am. Chem. Soc.* 106 (1984) 3695; Wang, Y. F., Sih, C. J. *Tetrahedron Lett.* 25 (1985) 4999.

To determine the constants, the diols, monoesters, and diesters were determined by GC analysis at a certain degree of conversion. The enantiomeric compositions of monoesters were determined by NMR analysis. As predicted, when the reaction was terminated at 71.5% conversion (a 50% conversion corresponds to the hydrolysis of one acetate group), the optical purity of the monacetate (S)-3 obtained was 96% (the isolated chemical yield was 53%).

The reported rotations of ((R)-3 of FIG. 3) are not in agreement with our values. The reported rotation of (R)-3 prepared through a lipoprotein lipase-catayzed hydrolysis of diacetate (4 of FIG. 3) was $[\alpha]_D^{20}$ −13.2 (c 3, EtOH), 91% ee. Breitgoff, D., Laumen, K., Schneider, M. P., *JCS Chem. Comm.* (1986) 1523. Another reported value was $[\alpha]_D^{25}$ +15.0 (c 2, CHCl$_3$) or −12.3 (c 1.8, EtOH); Kerscher, V., Kreiser, W., *Tetrahedron Lett.* 28 (1987) 531. Based on the rotation of the enantiomer prepared in the present reaction, the specific rotation of R-3 corresponds to 77% ee.

The kinetics of these irreversible transesterifications can be treated as similar to the kinetics of hydrolysis, and the equation developed by Sih et al. for use in prediction of ee vs. conversion in hydrolysis should be applicable here. Wang, Y. F., Chen, C. S., Girdaukas, G., Sih, C. J. *J. Am. Chem. Soc.* 106 (1984) 3695; Wang, Y. F., Sih, C. J. *Tetrahedron Lett.* 25 (1985) 4999. To determine the constants, the diols, monoesters, and diesters were determined by GC analysis at certain degree of conversion. The enantiomeric compositions of monoesters were determined by NMR analysis. Indeed, the kinetic constants for the transesterification of 2-0-benzylglycerol (2 of FIG. 3) using PSL were determined to be $\alpha = k_1/k_2 = 5.6$, $E_1 = k_3/(k_1+k_2) = 0.02$, $E_2 = k_4/(k_1+k_2) = 0.33$. Wang, Y. F., Chen, C. S., Girdaukas, G., Sih, C. J. *J. Am. Chem. Soc.* 106 (1984) 3695; Wang, Y. F., Sih, C. J. *Tetrahedron Lett.* 25 (1985) 4999.

To determine the absolute stereochemistry of the monoacetate, it was converted to 2,2-dimethyl-1,3-dioxolane-4-methanol (glycerol acetonide) according to the procedures of Suemune, H., Mizuhara, Y., Akita, H., Sakai, K. *Chem. Pharm. Bull.* 34 (1986) 3440–44; Hirth, G., Barner, R. *Helv. Chim. Acta* 65 (1982) 1059 (platelet-activating factor). The resulting glycerol acetonide was the "R" configuration based on rotation, indicating that the monacetate obtained had the "S" configuration. It has been reported that (R)-3 can be prepared from 2-0-benzylglycerol diacetate via a lipoprotein lipase-catalyzed hydrolysis. The same enantioselectivity in the hydrolysis of the diacetate (4 of FIG. 3) was observed with PSL and (R)-3 was obtained in 52% yield with 71% ee. When (S)-3 (91% ee) was suspended in phosphate buffer (0.1M, pH 7) at 28° C. without enzyme, the optical purity was found to decrease 2–2.5% per hour. These two irreversible enzymatic processes thus provide a new route to (R)-and (S)-3.

EXAMPLE 2—PPL-catalyzed transesterification of 2-N-benzyloxycarbonyl (Z) serinol (5 of FIG. 4) with vinyl valerate (1e of FIG. 2)

A solution of 2-N-benzyloxycarbonyl (Z) serinol (5 of FIG. 4) (225 mg, 1 mmol) and vinyl valerate (1e of FIG. 2) (512 mg, 4 mmol) in 22.5 mL of THF was incubated with 900 mg of PPL at 28° C. with stirring. After 11 hours, the reaction was terminated. The products were separated by silica gel column chromatography (ethyl acetate: n-hexane = 1:4→1:1) to afford 238 mg (77%) of monovalerate (R)-6 of FIG. 4, $[\alpha]^{23}_D$+3.2 (c 1.0, CHCl$_3$), and 75 mg of divalerate 7 of FIG. 4. Monovalerate (R)-6 of FIG. 4: $^1$H-NMR 0.91 (3H, t, J=7.2 Hz), 1.34 (2H, tq, J=7.2, 7.2 Hz), 1.60 (2H, tt, J=7.2, 7.2 Hz), 2.33 (2H, t, J=7.2 hz), 3.65 (2H, m) 3.94 (1H, m), 4.23 (2H, d, J=5.6 Hz), 5.11 (2H, s), 5.2 (1H, br), 7.36 (5H, s). Divalerate (7 of FIG. 4): $^1$H-NMR 0.91 (6H, t, J=7.2 Hz), 1.33 (4H, tq, J=7.2, 7.2 Hz), 1.59 (4H, tt, J=7.2, 7.2 Hz), 2.31 (4H, t, J=7.2, 7.2 Hz), $\delta$4.02≈4.30 (5H, m) 5.11 (7H, s), 5.05≈5.20 (1H, br), 7.36 (5H, s). To determine the optical purity of monovalerate R-6, R-6 was treated with (+)-2-methoxy-2-(trifluoromethyl)-phenylacetyl chloride [(+)-MTPA chloride] and the resulting (+)-MTPA ester (20 mg), which was analyzed by $^1$H-NMR spectroscopy in the presence of Eu(hfc)$_3$ (80 mg) to establish an enantiomeric excess (ee) greater than 97%. The relative intensities of benzylic methylene group at 4.8 (major) and 4.6 (minor) were measured for ee determination.

EXAMPLE 3—PSL-catalyzed transesterification of seudenol (8a in Table 2) with isopropenyl acetate (1a of FIG. 2)

Compound 8a has been used in natural product synthesis via radical-mediated cyclization. Stork, G., Sofia, M. J. *J. Am. Chem. Soc.* 108 (1986) 6826–28. A solution of isopropenyl acetate (0.44 mL, 4 mmol) and seudenol 8a (224 mg, 2 mmol) in 2 mL of n-hexane was mixed with 3 mg of PSL at 28° C. with stirring. After 20 hours, the amounts of seudenol acetate 8b and seudenol 8a were quantitatively determined to be 32:68 by GC analysis. The reaction mixture was worked up as usual and the products were separated by silica gel column chromatography (dichloromethane: n-hexane=1:3→1:0) to afford 91 mg (29.5%) of acetate 8b, $[\alpha]^{23}_D + 138.3$ (c 0.8, CHCl$_3$) and 138 mg (61.8%) of alcohol 8a, $[\alpha]^{23}_D - 26.7$ (c 1.5, CHCl$_3$). Acetate 8b: $^1$H-NMR 1.6≈2.0 (6H, m), 1.71 (3H, s), 2.03 (3H, s), 5.24 (1H, m), 5.47 (1H, m). The optical purity of monoacetate (+) 8b (9 mg) was determined to be 67% ee by $^1$H-NMR spectroscopy in the presence of Eu(hfc)$_3$ (57 mg). The relative intensities of the methyl group in double bond at 2.27 (major) and 2.31 (minor) were measured for ee determination. The alcohol (−)-8a was converted to the corresponding acetate by treatment of acetic anhydride in pyridine and then analyzed by the same procedure: ee=29%. 8a and 8b were assigned the designations of "S" and "R", respectively, based on their rotations compared to the reported values. Mori, K., Hazra, B. G., Pfeiffer, R. J., Gupta, A. K., Lindgren, B. S. *Tetrahedron Lett.* 43 (1987) 2249–54.

EXAMPLE 4—PPL-catalyzed transesterification of glycidol (9a in Table 2) with vinyl propionate (1d in FIG. 2)

To a 100 mL round bottomed flask was added glycidol (9a in Table 2) (2.3 g, 31 mmol), vinyl propionate (1d in FIG. 2) (7.0 g, 70 mmol), toluene (0.61 g) as an internal standard, and 80 mL of chloroform. The enzyme (PPL, 5 g) was suspended in the reaction mixture and the suspension was stirred. At 43% conversion (3.5 h), 5 g of celite was added to the suspension and the mixture was filtered. The filtrate was extracted with three 15 mL portions of distilled water and then washed once with 15 mL of saturated brine. The solvent was removed under reduced pressure and a yellow oil was obtained corresponding to pure glycidol propionate (9b in Table 4) (0.95 g, 23.2% yield from racemic glycidol). The optical purity as determined by Eu(hfc)$_3$ was 54%, while the optical rotation was found to be +15.2 (c 4, chloroform) corresponding to an optical purity of 53.5% (lit. for R ester is −28.4° C.)[25]. $^1$H-NMR 4.05 (dd, 1 H), 3.90 (dd, 1H), 3.24 (m, 1H), 2.85 (m, 1H), 2.65 (m, 1H), 2.35 (q, 3H), 1.15 (t, 3H), $^{13}$C-NMR 174.19, 64.83, 49.38, 44.65, 27.33, 9.01.

EXAMPLE 5—PPL-catalyzed transesterification of solketal (10a in Table 2) with vinyl esters In a representative procedure, 1 g of solketal (10a in Table 2) (7.5 mmol) and 2.3 g of vinyl acetate (1c in FIG. 2) (26.7 mmol) in 50 mL of chloroform was incubated with PPL (2 g) along with 0.5 g of hexane as an internal standard. After the reaction had proceeded to 40% conversion, the mixture was worked up as usual to give the ester with an optical purity of 42% by analysis with Eu(hfc)$_3$. The relative intensities of the methyl group of the isopropyl group at 2.63 (major) and 2.57 (minor) were measured to determine ee. In a similar manner the esterification was allowed to proceed to 80% conversion and the unreacted alcohol was isolated as described above. Solketal acetate 10b was found to have an optical purity of 65% ee. Solketal acetate 10b: $^1$H-NMR 4.40 (m, 1H), 4.05 (m, 3H), 3.72 (m, 1H), 2.07 (s, 3H), 1.35 (s, 3H).

EXAMPLE 6—PSL-catalyzed transesterification of 2-hydroxypropanal dimethyl acetal (11a in Table 2) and 3-hydroxybutanal dimethyl acetal (12a in Table 2)

Optically active 11a and 12a of Table 2 are useful as substrates in aldolase-catalyzed synthesis of novel sugars. Durrwachter, J. R., Wong, C- H. *J. Org. Chem.*, submitted. To a stirred solution of 2-hydroxypropanal dimethyl acetal (11a of Table 2) (480 mg, 4 mmol) and vinyl acetate (1c of FIG. 2) (20 mmol) in petroleum ether (20 mL) was added 9.6 mg of PSL. After the reaction had proceeded to 30%, the reaction suspension was treated as described in the general procedure. The products were separated on a silica gel column (petroleum ether: ethyl acetate=9:1→3:1). 2-acetoxy-propanal dimethyl acetal 11b: $^1$H-NMR (CDCl$_3$); 1.16 (3H, d, J=5.5 Hz); 2.00 (3H, s); 3.33 (3 H, s); 3.36 (3H, s); 4.20 (1H, d, J=5.5 Hz); 4.80≈4.99 (1H, m).

To determine the optical purity of 2-acetoxypropanal dimethyl acetal 11b it was transformed to (+)-MTPA ester by hydrolysis with NaOH followed by reaction with (+)-MTPA-Cl. The resulting (+)-MTPA ester was analyzed by $^1$H-NMR spectroscopy. The relative intensities of the methine group at 4.32 and 4.22 were used for ee determination. The same procedure was used for the resolution of 12a, except that vinyl valerate (1e of FIG. 2) and CCL were used. The methine group shifts of the MTPA ester at 4.38 and 4.17 ppm were used for ee determination.

EXAMPLE 7—PPL catalyzed transesterification of (±)-2-octanol (13a of Table 2) with vinyl acetate (1c in FIG. 2)

520 mg (4 mmol) of 2-octanol (13a of Table 2) was dissolved in 8 mL of benzene along with 240 μL of dodecane as an internal standard. Two equivalents of vinyl acetate (1c in FIG. 2) were added along with 520 mg of PPL. The suspension was stirred at 28° C. After the reaction had proceeded to 37%, the reaction suspension was worked as described in the general procedure. The products were separated on a silica gel column. The optical purities of isolated ester 2-octyl acetate (13b in Table 2) and 2-octanol (13a in Table 2) were determined by $^1$H-NMR spectroscopy in the presence of Eu(hfc)$_3$ (12 mg of acetate, or alcohol was added 84 mg or 72 mg of Eu(hfc)$_3$, respectively). The relative intensities of the methyl groups near the chiral center at 8.72 (major) and 8.64 (minor) (alcohol) and 4.3 (major) and 4.42 (minor) (ester) were used for ee determination. The ester was found to have an optical purity of 98% ee. In a similar manner, the esterification was allowed to proceed at 58% conversion and the unreacted alcohol was isolated. The alcohol was found to have an optical purity of >98% ee. The specific rotation of unreacted alcohol was +8.7° (c 1.0, CDCl$_3$) or +8.9° (neat). Authentic (S)-2-octanol from Aldrich: $[\alpha]^{17}$ +9° (neat). This result confirms that the unreacted alcohol has the "S" configuration. (R)-2-octyl acetate 13b: $^1$H-NMR (CDCl$_3$): 0.88 (3H, t, J=6.8 Hz); 1.20 (3H, d, J=6.2 Hz); 1.27 (8H, s); 1.41≈1.66 (2H, m), 2.02 (3H, s); 4.88 (1H, qt, J=6.2 Hz and 12.6 Hz).

EXAMPLE 8—PPL-catalyzed transesterification of sulcatol (14a in Table 2) with vinyl acetate (1c of FIG. 2)

Compound (S)-14a (Table 2) is a useful pheromone, which has been prepared via lipase-catalyzed transesterification of the racemic alcohol using trichloroethyl propionate and trifluoroethyl laurate. Tambo, G. M. R., Schar, H-P., Busquets, X. F., Ghisalba, O. *Tetrahedron Lett.* 27 (1986) 5705-10; Belan, A., Bolte, J., Fauve, A., Gourey, J. G., Vaschambre, H. *J. Org. Chem.* 52, 256-60 (The latter is for synthesis of (S)-14a), Stokes, T. M., Oehlschlager, A. C. *Tetrahedron Lett.* 28 (1987) 2091-94 (trifluoroethyl laurate), and via alcohol dehydrogenase-catalyzed reduction of the ketone precursor. Tambo, G. M. R., Schar, H-P., Busquets, X. F., Ghisalba, O. *Tetrahedron Lett.* 27 (1986) 5705-10; Belan, A., Bolte, J., Fauve, A., Gourey, J. G., Vaschambre, H. *J. Org. Chem.* 52, 256-60 (The latter is for synthesis of (S)-14a). All of these processes give (S)-14a with >98% ee. The procedure described here using readily available vinyl acetate is faster and the product is easier to isolate.

513 mg (4 mmol) of sulcatol (14a in Table 2) was dissolved in 8 mL of benzene along with 240 μL of dodecane as an internal standard. Two eq (8 mmol) of vinyl acetate (1c of FIG. 2) was added along with 512 mg of PPL. The suspension was stirred at 28° C. After the reaction had proceeded to 27%, the reaction was terminated and treated by the general procedures already described. The products were separated by silica gel column chromatography (CH$_2$Cl$_2$: n-hexane=0:1→1:4) giving acetate ester (14b of Table 2) and unreacted alcohol 14a. The optical purities of isolated sulcatol acetate and sulcatol were determined by $^1$H-NMR spectroscopy in the presence of Eu(hfc)$_3$. The relative intensities of methyl group near chiral center at 9.75 (major) and 9.56 (minor) (alcohol) and at 4.92 (major) and 5.02 (minor) (ester) were used for ee determination. The ester was found to have 98% ee.

In a similar manner, the esterification was allowed to proceed to 62% conversion and the unreacted sulcatol was isolated. The ee of unreacted sulcatol was found to be >98%. The specific rotation of unreacted alcohol was +15.1 (c 2, b, EtOH). [(S)-sulcatol; [α]$^{25}$$_D$+15.6° (c 0.015, EtOH)]. This result confirms that the unreacted alcohol had the "S" configuration. The $^1$H-NMR spectrum and the optical rotation of 14b corresponded to that reported for the "S" configuration of 14b. Tambo, G. M. R., Schar, H-P., Busquets, X. F., Ghisalba, O. *Tetrahedron Lett.* 27 (1986) 5705-10; Belan, A., Bolte, J., Fauve, A., Gourey, J. G., Vaschambre, H. *J. Org. Chem.* 52, 256-60 (The latter is for synthesis of (S)-14a).

EXAMPLE 9—PPL-catalyzed transesterification of ferrocenylethanol (17a of Table 2) and vinyl propionate (1d of FIG. 2) in toluene The resolution of ferrocenylethanol (17a of Table 2) represents an interesting example of enzyme-catalyzed kinetic resolution of chiral organometallic compounds. The ester (17b of Table 2) in aqueous ethanol decomposes via solvolysis to ferrocenylethyl ethyl ether and 17a. Gokel, G. W., Marquarding, D., Ugi, I. K. *J. Org. Chem.* 37 (1972) 3052-58. The acetate was subjected to SN$_1$ and SN$_2$ displacement. When the enzymatic resolution was carried out in aqueous solution, racemic 17a and 17b were obtained. The resolution therefore must be carried out in non-polar aprotic solvents such as toluene.

A mixture of ferrocenylethanol (17a of Table 2) (1 g, 4.4 mmol), vinyl propionate (1d of FIG. 2) (6 mL, 52.8 mmol), and PPL (3 g) in toluene (25 mL) was shaken for 6 days. The reaction was stopped at ≈ 40% conversion (determined by NMR, based on the ratio of the methyl doublet of the reactant alcohol to that of the product ester). The mixture then was filtered to remove the enzyme and the filtrate was evaporated to give a mixture of products (0.72 g) which were separated by silica gel chromatography with hexane: ethyl acetate=5:1 v/v as the solvent system to give ferrocenylethyl propionate 17b ([α]$_D$−11.2 (c 1, EtOH)).

Ferrocenylethanol 17a (0.31 g, mp 70°-71° C., [α]$_D^{25}$+25.9 (c 1, benzene), lit$^{21}$+30.1) prepared by a similar reaction proceeded to 60% conversion. The enantiomeric excesses of ferrocenylethanol 17a and ferrocenylethyl propionate 17b were determined to be 84% and 84%, respectively, with H-NMR in the presence of Eu(hfc)$_3$ (the methyl doublet of ferrocenylethanol 17a at 3.35 ppm and the methyl triplet of the acyl portion of the ester 17b at 2.82 ppm were measured). The configurations were determined to be "S" for ferrocenylethanol 17a and "R" for ferrocenylethyl propionate 17b based on the rotation compared to the reported values. Gokel, G. W., Marquarding, D., Ugi, I. K. *J. Org. Chem.* 37 (1972) 3052-58. Ferrocenylethyl propionate 17b: $^1$H-NMR 1.10 (t, 3H), 1.55 (d, 3H), 2.30 (q, 2H), 4.2-4.44 (m, 9H), 5.80 (q, 1H). $^{13}$C-NMR (CDCl$_3$)9.22, 20.12, 27.92, 65.95, 67.92, 68.24, 68.70, 88.15, 173.89. The NMR data of ferrocenylethanol 17a were the same as reported. Gokel, G. W., Marquarding, D., Ugi, I. K. *J. Org. Chem.* 37 (1972) 3052-58. The acetate was subjected to SN$_1$ and SN$_2$ displacement. When the enzymatic resolution was carried out in aqueous solution, racemic 17a and 17b were obtained.

Structural Effect of Enol Esters

To compare the structural effect of different enol esters on the rate and stereoselectivity of the enzymatic transesterification, the resolution of solketal (10a of Table 2) using CCL as catalyst was performed. The results are shown in Table 3.

TABLE 3

Reaction rates and enantioselectivity of CCL-catalyzed transesterification of 10a with various acylating reagents[a] and of PPL-catalyzed reactions with 13[b].

| Ester | substrate | enzyme | Rel. Rate | % conversion | E[c] |
|---|---|---|---|---|---|
| CH$_3$CO$_2$Et | 10a | CCL | 1[d] | 16 | 1.2[e] |
| 1a | 10a | CCL | 20 | 42 | 1.4 |
| 1b | 10a | CCL | 8 | 44 | 2.7 |
| 1c | 10a | CCL | 62 | 37 | 1.4 |
| 1d | 10a | CCL | 122 | 53 | 2.0 |
| 1e | 10a | CCL | 13 | 23 | 3.1 |
| CH$_3$CO$_2$CH$_2$CF$_3$ | 10a | CCL | 1.5 | 34 | 1.4 |
| CH$_3$CO$_2$Et | 10a | CCL | 0.4[f] | — | — |
| 1a | 10a | CCL | 1700[g] | — | — |
| 1c | 13a | PPL | 5.5 | 58 | 96 |
| CH$_3$CO$_2$Et | 13a | PPL | 0.1 | 58 | 80 |

TABLE 3-continued

Reaction rates and enantioselectivity of CCL-catalyzed transesterification of 10a with various acylating reagents[a] and of PPL-catalyzed reactions with 13[b].

| Ester | substrate | enzyme | Rel. Rate | % conversion | E[c] |
|---|---|---|---|---|---|
| H$_2$O | 13b | PPL | 60 | 58 | 90 |

[a]Reaction condition: the alcohol substrate (2 mmol) was dissolved in benzene (4 mL) along with 120 μL of dodecane as an internal standard. The acylating agent (2 eq) and CCL (265 mg) were added and the suspension was stirred at 28° C. At various intervals, the degree of conversion was determined by GC (20 m DB-5 megabore column; initial temperature, 80° C.; initial time, 1 minute; gradient, 10° C./min; flow rate 15 mL/min). After a certain degree of conversion, the reaction was terminated by filtration and the filtrate was evaporated. The residue was purified on a silica gel column (CH$_2$Cl$_2$:n-hexane = 1:3→1:0) to obtain the ester product. The optical purity of the product was determined by $^1$H—NMR in the presence of Eu(hfc)$_3$ (10 mg of acetate, propionate or pentanoate was added 40 mg, 40 mg or 28 mg of the shift agent, respectively).
[b]Conditions: for transesterification, PPL (520 mg), solvent (8 mL), substrate (4 mmol), acylating reagent (2 eq), temperature (28° C.). For hydrolysis, the same as above except that phosphate (0.1M, pH 7) was used as solvent.
[c]A measure of enantioselectivity determined by the method reported previously: Chen, C.-S.; Fujimoto, Y.; Girdaukas, G.; Sih, C. J. J. Am. Chem. Soc. 1982, 104, 7194.
[d]The initial rate was 0.8 μmol ester product formed per min per g of enzyme.
[e]The E value was obtained without considering the reverse reaction.
[f]The tributyl tin ether of glycerol acetonide was used as substrate.
[g]No transesterification was observed in 0.05M phosphate buffer at pH 7. The rate of hydrolysis of 1a was measured.

The reaction rate of enol ester was 10–100 times faster than ethyl acetate. Among the enol esters, vinyl esters reacted faster than isopropenyl esters and vinyl propionate was faster than vinyl acetate, but enol valerates were slower than enol acetates. The reaction rate of transesterification using different acylating reagents was compared to that of hydrolysis. As indicated in the resolution of 13 using PPL as catalyst, the relative rates for the hydrolysis of 13b and transesterification of 13a with vinyl acetate and ethyl acetate were found to be 600:55:1. The longer enol esters gave higher enantioselectivity. The lower selectivity in the ethyl acetate reaction may be due to the reversible nature of the reaction.

Effect of Organic Solvent

The effect of organic solvent on the CCL-catalyzed transesterification also was examined. As shown in Table 4, the rate of transesterification of glycerol acetonide (solketal) and isopropenyl acetate was slower in more polar solvents than in less polar solvents.

TABLE 4

Effect of organic solvents on CCL-catalyzed transesterfications of glycerol acetonide and 1a

| Reaction Solvent[a] | Relative Rate | E |
|---|---|---|
| Benzene | 50 | 1.4 |
| Isopropanyl acetate | 37 | 1.6 |
| Chloroform | 9 | 1.5 |
| Tetrahydrofuran | 1[b] | 1.5 |

[a]Reaction conditions are the same as those described in Table 2.
[b]The initial rate was 0.32 μmol ester formed per min per gram of enzyme.

All lipases tested were catalytically active in pyridine but inactive in DMF. In a study of the solvent effect on the activity of lipases in organic solvents, it was found that the rate of CCL-catalyzed acylation was enhanced in the presence of benzene.

Many valuable chiral synthons were prepared in high optical purity via lipase-catalyzed transesterification. The combination of two irreversible enzymatic processes, ester hydrolysis and ester synthesis, enabled effective syntheses of a number of optically active monoesters and alcohols in both enantiomeric forms, even with a moderately enantioselective enzyme. The same procedures also can be applied to the resolution of chiral ferrocenylethanol to prepare both enantiomers, a process which is impossible to accomplish in aqueous solution.

Lipases and cholesterol esterase were found to catalyze enantioselective ester syntheses in various organic media. The leaving groups (acetone and acetaldehyde) of enol esters used in the processes are volatile and easy to remove, making the product separation very simple. With regard to the rate of transesterification, vinyl esters were about 20–100 times faster than ethyl esters and about 5 times faster than isopropenyl esters, and generally the long chain esters were faster than short chain esters. As compared to lipase-catalyzed hydrolysis, vinyl esters reacted 10 times slower. Because the transesterification reaction is carried out in neutral apolar organic solvents, this procedure is suitable for acid-, base- or water sensitive substances.

Regioselective Acylations of Sugars and Their Derivatives

The methyl and higher glycosides of hexoses and pentoses are sufficiently soluble in pyridine or other less polar media such that the enzymatic acetylations of these compounds can be accomplished with lipase-catalysis. Stronger solvents such as N,N-dimethylformamide (DMF), dissolve many otherwise insoluble sugars but they also render the lipases inactive. Riva, S., Chapineau, J., Kieboom, A. P. G., Klibanov, A. M. J. Am. Chem. Soc. 110 (1988) 584–589. We have found that Protease N (neutral protease from Amano International Enzyme Company) will utilize enol esters as acyl donors. This enzyme also retains its catalytic activity in dry DMF.

Summaries of some of the data obtained with hexoses (Table 5), furanosides (Table 6), and nucleosides (Table 7) are shown hereinafter. Selected specific as well as general procedures for acetylation of sugars and their derivatives also are disclosed.

TABLE 5

Enzyme-catalyzed acetylation of hexoses and their derivatives using enol esters.

18a R = H
18b R = Ac

19a R = H
19b R = Ac

19a R = H
19b R = Ac

| Compound | ENZ | Enol ester | Conversion (%) | Regioselectivity (%) | Isolated Yield (%) |
|---|---|---|---|---|---|
| 18a | CCL | 1c | 30 | >98 | 23 |
| 19a | PN | 1a | 60 | >90 | 49 |
| 20a | PN | 1a | 85 | >90 | 73 |

TABLE 6

Lipase-catalyzed acetylation of furanosides.

| | $R_1$ | $R_{1'}$ | $R_2$ | $R_{2'}$ | $R_3$ | $R_{3'}$ |
|---|---|---|---|---|---|---|
| 21 | (H, | OMe) | H | OH | H | OH |
| 22 | H | OMe | OH | H | H | OH |
| 23 | (H, | OMe) | H | OH | OH | H |
| 24 | (H, | OMe) | H | H | H | OH |

Parentheses indicate a mixture of anomers.

| Substrate | Product Yields[a] (%) 2-OAc | 3-OAc | 5-OAc | Regioselectivity % |
|---|---|---|---|---|
| Methyl α,β-D-ribo-furanoside, 21 | 0 | 0 | 75–80[b] | 100 |
| Methyl α-D-arabino-furanoside, 22 | 0 | 0 | 75–80[b] | 100 |
| Methyl α,β-D-xylofur-anoside, 23 | 0 | 0 | 80–85[b] | 100 |
| Methyl 2-deoxy-α,β-D-ribofuranoside, 24 | — | 17[c] | 39[d] | 78–100[e] |

[a] Yields reported are for anomeric mixtures.
[b] The anomeric products were separated to facilitate spectroscopic identification.
[c] The product obtained was methyl 3-O-acetyl-2-deoxy-β-D-ribofuranoside.
[d] The product consisted of a 9:1 mixture of α:β anomers.
[e] Regioselectivity was calculated based upon the individual anomers.

EXAMPLE 10—CCL-catalyzed transesterification of methyl β-D-glucopyranoside (18a of Table 5) with vinyl acetate (1c of FIG. 2)

Methyl β-D-glucopyranoside (18a of Table 2) (388 mg, 2 mmol) and vinyl acetate (1c of FIG. 2) (4 mmol) were dissolved in 12 mL of benzene-pyridine (2:1). Then 388 mg of CCL was added, and the suspension was stirred at 28° C. After 24 hours, an additional 388 mg of CCL was added, and this was repeated after 48 hours. The suspension was stirred at 28° C. for 5 days; then worked up as usual to afford methyl 6-O-β-D-glucopyranoside 18b as a solid, which was crystallized from ethyl acetate-n-hexane; m.p. 129°≈130° C.; $[\alpha]^{25}_D -27.1$ (c 1.4, CH$_3$OH); $^1$H-NMR (CD$_3$COCD$_3$); 2.02 (3H, s); 2.98 (1H, s); 3.13≈3.25 (1H, m), 3.3≈3.55 (3H, m), 3.45 (3H, s), 4.15≈4.25 (2H, m); 4.30≈4.45 (3H, m); $^{13}$C-NMR (CD$_3$COCD$_3$); 104.56 (C1), 74.29 (C2), 77.36 (C3), 70.85 (C4), 74.33 (C5), 64.01 (C6), 20.42 and 170.69; (acetyl), 56.39 (methoxy).

Regioselective Acetylation of Methyl Pentofuranosides

The following general procedure was used for the substrates listed in Table 6.

To a solution of 1.64 g (10 mmol) of methyl pentofuranoside in a 24 mL of dry tetrahydrofuran containing a trace of hydroquinone was added 4.7 mL (50 mmol) of vinyl acetate (1c) and 5.0 g of porcine pancreatic lipase (PPL). The mixture was shaken in the dark at 37° C. on an orbital shaker at 250 rpm. The reaction was monitored by TLC. After 24–60 h the solution was filtered and the solids washed with fresh tetrahydrofuran. The filtrate and washings were evaporated in vacuo and the residue purified by silica gel chromatography using either chloroform-methanol or ethyl acetate-hexane mixtures as eluent. The regioselectivities and yield ranges for the specific reactions are listed in Table 6.

Protease-Catalyzed Reactions

Protease N obtained from Amano International Enzyme Co. was used on the following reactions. Other highly stable proteases, such as proteases obtained from thermophillic organisms or genetically engineered stable proteases, also could be used in the following reactions. The crude commercial preparation was dissolved in 0.1 M phosphate buffer, pH 7.8 (2 g/35 mL) and lyophilized. The dry powder that was obtained was pulverized with a mortar and pestle prior to use.

REGIOSELECTIVE ACYLATION OF SUGAR

EXAMPLE 11—Preparation of 2-acetamido-6-O-acetyl-2-deoxy-D-mannopyranose

Protease N from *Bacillus Subtillis* (obtained from Amano) (2 g) was dissolved in 0.1 mol NaH$_2$PO$_4$ (35 mL), and the resulting solution was stirred for 15 min. The pH was then adjusted to 7.8 with 8.0 NaOH and the solution was freeze-dried. This freeze-dried preparation was used in the synthetic procedure. N-acetyl-β-D-mannosamine monohydrate (Sigma) (478 mg, 2 mmol) was suspended in anhydrous N,N-dimethylformamide (2 mL). Isopropenyl acetate (600 mg, 6 mmol) was added followed by the enzyme preparation (600 mg). The suspension was shaken at 45° C. and monitored by TLC (silica gel; EtOAc:MeOH:H$_2$O = 100:10:1). After 44 h, the suspension was filtered and the enzyme washed with methanol (2×3 mL). The solvents were evaporated under vacuum at 40° C. to give a yellow syrup. This syrup was fractionated on a silica gel column (45 g) eluted with EtOAc/MeOH/H$_2$O = 100/10/1. Two products were obtained: the first with a higher R$_f$ corresponded to a triacetate compound (30 mg, 10%). The second (major) product was obtained as an amorphous white solid which, upon analysis was revealed to be 2-acetamido-6-O-acetyl-2-dexoy-D-mannopyranose. (384 mg, 73%): $^1$H-NMR (D$_2$O/p-dioxane = 3.57 ppm) δ4.93 (s, H 1α), 4.84 (s, H 1β), 4.29–4.02 (m, 5H), 3.87 (dd, H 3α), 3.70–3.27 (m, 3H), 1.95, 1.91, 1.88, and 1.87 (4 s, 6H, acetal); $^{13}$C-NMR (D$_2$O/p-dioxane = 67.46 ppm) δ176.60, 175.67, 174.96, and 174.92 (all carbonyls), 94.05 (c 1β), 93.97 (C 1α), 74.78 (c β), 72.72 C β), 70.57 (C 5α), 69.43 (C α), 67.94 (C α), 67.78 C β), 64.61 (C 6α), 64.36 (C 6β), 54.84 (C 2β), 54.18 (c 2α); α/β=76/24; mp 47°–51° C.; $[\alpha]^{24}_D +15.9°$ (c 1.13 H$_2$O). Anal. Calcd for C$_{10}$H$_{16}$NO$_7$: C, 45.80; H, 6.15; N, 5.34. Found: C, 45.89; H, 6.20; N, 4.95.

REGIOSELECTIVE ACYLATION OF NUCLEOSIDES

EXAMPLE 12—General Procedures

The following general procedures were used in performing the regioselective acylation of nucleosides listed in Table 7:

1 mmol of nucleoside was dissolved in 2–4 mL of dry DMF and warmed. The solution was cooled to 45° C. and 1.1 mL (10 eq) of isopropenyl acetate and 260 mg of pulverized protease N were added. The suspension was shaken at 45° C. After the appropriate times, as indicated in Table 7, the reaction mixture was filtered and the filtrate was evaporated to dryness. The residue was purified by silica gel chromatography using mixtures of ethyl acetate:ethanol:water as the eluent for the times indicated. The isolated products were obtained in the yields shown in Table 7.

Table 7 indicates that, where acetylation occurred, the monoacetyl derivative was predominantly formed. The preferential formation of the monoacetyl derivative indicates that the nucleoside was acetylated at the primary (5') hydroxyl group.

TABLE 7

Selective Enzymatic Acetylations of Nucleosides and Sugars in Anydrous Dimethyl-Formamide

| Substrate | Enzyme | Time (days) | Monoacetyl (%) | Diacetyl (%) | Starting Material (%) |
|---|---|---|---|---|---|
| Guanosine | PN | 5 | 0 | 0 | 100 |
| Adenosine | PN | 1.75 | 40 | 0 | 60 |
| " | PN | 5 | 65 | <5 | 30 |
| 2-Deoxy adenosine | PN | 2 | 50 | — | — |
| " | PN | 4 | 80 | — | — |
| Uridine | PN | 1.75 | 50 | 0 | 50 |
| " | PN | 5 | 80 | <5 | 15 |
| " | PN(pyr) | 5 | 60 | 0 | 40 |
| " | PN(THF) | 5 | 0 | 0 | 100 |
| " | PPL(pyr) | 3 | >95 | 0 | <5 |
| " | PPL(THF) | 3 | >95 | 0 | <5 |
| Cytidine | PN | 1.5 | 60 | 0 | 40 |
| " | PN | 3 | 80 | <5 | 15 |
| " | S | 3 | 0 | 0 | 100 |
| 2-Deoxycytidine | PN | 2 | 60 | — | — |
| " | PN | 4 | 80 | — | — |
| Thymidine | PN | 1.5 | 90 | 0 | 10 |
| " | S | 1.5 | 0 | 0 | 100 |
| Methyl 2-deoxy-D-ribofuranoside | PN | 2 | 70 | — | — |

PN = protease N [Amano]
S = subtilisin BPN
PPL = porcine pancreatic lipase The simplicity of this irreversible transesterification makes the operation useful for the preparation of chiral alcohols or esters that may be difficult to prepare by other means.

ENZYMATIC RESOLUTION OF HYDROXYCYCLOPENTENONES UTILIZING LIPASE

Lipase catalyzed reactions were utilized in the resolution of hydroxycyclopentenones as illustrated in the following reaction schemes, illustrating specific embodiments of the present invention.

Using the procedure described herein, resolution of hydroxy-cyclopentenones was achieved. Specifically, hydroxy-alkyl-carbonyl-alkyl, alkenyl or alkynyl cyclopentenones, alternatively including a heteroatom in the side chain, are suitable for practice of the described method. The compounds can be described illustratively by the formulae:

wherein x represents alkyl, alkenyl or alkynyl, of from 2 to 10 carbon atoms, alternatively including a heteroatom, namely S or O, at the 2, 3, 4, 5, 6, 7, 8 or 9 position; and R is $CH_2OR_1$ or—$CO_2R_2$, wherein $R_1$ is hydrogen, alkyl of 1 to 6 carbon atoms, tetrahydropyranyl, ethoxyethyl, or acyl, wherein $R_2$ is alkyl of 1 to 6 carbon atoms.

Practical and presently preferred embodiments of the method are described in the following examples which are not intended to be limiting.

Several lipases which are available commercially were utilized, namely: Candia cylindracea (CC), pseudomonas Species (P.Sp.), porcine pancreatic lipase (PPL), all from Sigma Chemical, and Amano P, ANL, Aspergillus niger, ChE, Cholesterol Esterase, all from Amano Co. The role of solvent with respect to both rate of reaction and extent of kinetic resolution was also studied. The conversions were monitored utilizing normal phase HPLC on silica gel (Zorbax sil) and the optical purities of products were analyzed using HPLC on chiral stationary phase (Chiracel OD column).

Scheme 1

SCHEME 2

Two critical challenges were considered: a) enone (1S) which has the undesired (S)-configuration must be inverted with high stereospecificity to give the necessary (R)-enone (1R); b) over half of the product from the lipase reaction was 11-OAc-enone, (2R) which was predominantly (94%) the (R)-isomer. Methodology for enrichment of this material to usable optical purity (i.e. 98%) was desirable.

With respect to the first point, it was found that enone (1S) could be converted to (1R) via Mitsunobu chemistry.

In the present case, when (1S) of 99.9% (S) purity was submitted to Mitsunobu conditions (Bull. Chem. Soc. Japan 44 3427, 1971) using formic acid as nucleophile and then immediate hydrolysis of the formate ester intermediate, a 91–94% chromatographed yield of inverted enone (1R) was obtained which was 99.3–99.6% (R) isomer. Therefore, only a maximum of 0.3 to 0.5% of racemization had occurred. This product was then converted to its triethyl silyl derivative, (3) in 94% yield after chromatography. Again, HPLC analysis on Chiracel OD column showed this material to be of identical optical purity to its precursor (99.3% R).

This enzymatic resolution method, coupled with the Mitsunobu alcohol inversion technology described here enables the preparation of either antipode of the optically pure alcohol desired.

The following important features of the described process should be noted. No special apparatus or inert atmosphere are required for the lipase reactions since all reactions were carried out in organic solvents in the absence of water. A 0.1–0.2 kg scale kinetic resolution of racemic enone was easily performed in the laboratory. The four hydroxy enones shown above were also submitted to enzymatic resolution using PPL in vinyl acetate as described for compound (1). Greater than 92% ee (unoptimized) was achieved in all cases after 4 days reaction time. Chromatography is a *necessary* purification process for each hydroxy to acetate transformation since failure to remove acetate from the alcohol quantitatively will lead to effective racemization. All chemical and enzymatic reactions take place with a high degree of stereoselectivity and in high yield. Three batches of target Triethyl Silyl (3) were prepared: 40.25 g (99.3% R), 6.59 g (99.7% R) and 8.90 g (99.4% R).

It was found that all of the lipases were selective in acylating the R-isomer of the starting enone compound (1) with *Pseudomonas* species lipase being the most active catalyst. Using *Pseudomonas* species lipase, commercially available as Amano-P from Amano Co. as the enzyme source, relative rates of reaction were examined in five solvent systems using isopropenyl acetate as the acylating agent. Use of t-butyl methyl ether (TMBE) and aromatic solvents gave the highest rates. In addition to the lipase PPL, *Candida cylindracea* (CC) lipase and a *pseudomonas* Sp. (Amano-P) were studied both as their free powders and also immobilized on Amberlite XAD-8 resin, SIGMA Chem Co. In all cases, reaction at room temperature or 50° C. were extremely slow, usually <10% conversion after 5 days. However, with PPL immobilized on XAD-8 resin, a 25% conversion was achieved after 5 days at room temperature. Optimum conditions were established when excess vinyl acetate was employed in place of isopropenyl acetate and no solvent was used. Under these conditions reactions could be run at room temperature, were much faster and proceeded smoothly in 3–5 days. Moreover, the side products observed when isopropenyl acetate was employed as the acylating agent (due to interference by the methyl ester) were eliminated. The viability of the process was demonstrated on a 100 g scale.

A two-step process in which the acetate is removed by a purely chemical means and the recovered alcohol then resubmitted to the lipase acylation conditions was found to be most advantageous.

Referring to Scheme 2, when (2R) was treated with 2 equiv. of guanidine in CH$_3$OH, very rapid, clean conversion to the desired compound (1R) was observed in less than 5 minutes at 0° C. In fact, when only 0.25 equiv. of guandine were employed, the reaction profile and rate were identical to the stoichiometric case and compound (1R) (93% R) was recovered in 75–77% yield after chromatography. When this material was resubmitted to the action of PPL in vinyl acetate for 2 days, a 90% yield of compound (2R) was obtained with an enantiomeric excess of 99.6% (this represents a 98% conversion of available (R) alcohol (1R)). Deacylation via guanidine in methanol as described above provided the target (R)-enone (1R)). HPLC showed no racemization again during acetate removal. These results allow for complete conversion of both antipodes of (SC-37321) into chiral enone and all recovered non-enriched intermediates can be recycled to high optical purity (see Scheme 2).

EXPERIMENTAL SECTION

Column chromatography separations were performed by using Merck SiO$_2$60 silica gel with ethyl acetate/hexane mixtures as eluants. TLC analyses were performed on Merck SiO$_2$60 F254 precoated glass plates and were visualized by charring with phosphomolybodic acid in ethanol. Melting points (differential scanning calorimetry) were obtained on a Dupont 9900 Thermal Analyzer. NMR were recorded at room temperature in CDCl$_3$ using a General Electric QE-300 or Varian XL-400 spectrometer with TMS as internal standard. HPLC analyses were performed on Chiralcel OD, OA, or OC columns employing a chiral stationary phase (Daicel Chemical Industries) on a Waters Associates Model 590 solvent deliver system with Waters Intelligent Sample Processor (WISP). Optical rotations were measured with a Perkin-Elmer 241 polarimeter. IR spectra were recorded (as solutions in chloroform) on a Perkin-Elmer 681 spectrometer. CD spectra were recorded on a JASCO J-20 ORD/CD spectropolarimeter. UV spectra recorded (in CH$_3$OH) on a Beckman DU-7HS UV-Vis spectrophotometer.

Diethyl azodicarboxylate, triphenylphosphine, formic acid, guanidine carbonate, triethylsilyl chloride, sodium spheres were purchased from Aldrich and used without purification. Lipases: candida cylindracea (CC), porcine pancreatic lipase (PPL), pseudomonas species (PSp.) were purchased from Sigma Chemical Co. Amano P lipase, generally known as *Pseudomonas species lipase*, was purchased from Amano Co. Isopropenyl acetate and vinyl acetate were purchased from Aldrich and fractionally distilled prior to use. All solvents were purchased from Burdick and Jackson and were reagent grade. CH$_3$OH was distilled from Mg; DMF was distilled at reduced pressure from magnesium sulfate, benzene and toluene were azeotropically distilled, chloroform was distilled from P$_2$O$_5$ and t-butyl methyl ether was distilled from benzophenone ketyl (all under inert atmosphere).

EXAMPLE 13

Preparation of Methyl 7-[3R-(acetyloxy)-5-oxo-1-cyclopenten-1-yl]-4Z-heptenoate (2R) and Methyl 7-(3S-hydroxy-5-oxo-1-cyclopenten-1-yl)-4Z-heptenoate (1S) via enzymatic resolution A mixture of 100.0 g of (0.42 mole) (±)methyl 7-(3-hydroxy-5-oxo-1-cyclopenten-1-yl)-4Z-heptenoate (1), 100 g of porcine pancreatic lipase (14M units) and 2.5 L of distilled vinyl acetate were vigorously stirred at room temperature for 4 days. An additional 50-g portion of porcine pancreatic lipase was added and the mixture was stirred for one more day. The course of the reaction was monitored via HPLC on Chiralcel OD using 93:7 hexane:isopropanol as eluant until the enantiomeric excess of unreacted 3(S) alcohol was >99.8%. The crude mixture was then treated with 50 g of diatomaceous earth and filtered through a bed of diatomaceous earth. The filter cake was washed with 1.5 L of methylene chloride. The combined filtrates were concentrated under reduced pressure to give approximately 119 g of product mixture which contains predominantly 3(R)-acetate and 3(S) alcohol having R$_f$ values of 0.25 and 0.49 respectively on TLC using 80% ethyl acetate/hexane. The product was chromatographed on silica gel using a solvent gradient of 50% to 100% ethyl acetate/hexane to give 50.5 g (43%) of (R) enriched methyl 7-[(3R-acetyloxy)-5-oxo-1-cyclopenten-1-yl]-4Z-heptenoate (2R) $^1$H NMR (CDCl$_3$): δ7.10 (m, 1H, C$_2$H), 5.67 (m, 1H, C$_3$H), 5.30 (m, 2H, olefinic H), 3.68 (S, 3H, OCH$_3$), 2.86 (dd, 1H, C$_{4\beta}$H) J=6.5, 18.5 Hz, 2.36 (dd, 1H, C$_{4\alpha}$H) J=2.1, 18.5 Hz, 2.4–2.25 (m, 8H, CH$_2$); $^{13}$C NMR (CDCl$_3$) δ204.3, 173.1, 170.3, 151.8, 148.8, 129.4, 128.6, 71.3, 51.3, 41.3, 33.7, 24.7, 24.3, 22.6, 20.7 ppm; IR (CHCl$_3$) 3030, 3010, 1735, 1720, 1440, 1370, 1230 cm$^{-1}$; [α]$_D^{20}$+45.4° (−634.3° at 365 nM) (c 1.080 g/dL, CHCl$_3$); UV (CH$_3$OH) V$_{max}$=220 nM; Anal. calc'd. for C$_{15}$H$_{20}$O$_5$=C, 64.27; H, 7.19 Found: C, 64.24; H, 7.32 and 35.1 g (35%) of methyl 7-(3S-hydroxy-5-oxo-1-cyclopenten-1-yl)-4Z-heptenoate (1R) $^1$H NMR (CDCl$_3$) δ7.10 (m, 1H, C$_2$H), 5.24 (m, 2H, olefinic), 4.93 (m, C$_3$H, 1H), 4.05 (b, 1H, OH), 3.68 (S, 3H, OCH$_3$), 2.80 (dd, 1H, C$_{4\beta}$H) J=6.0, 18.5 Hz, 2.4–2.2 (m, C$_{4\alpha}$H+CH$_2$'S, 9H); $^{13}$C NMR δ207.1, 174.1, 157.6, 146.9, 130.1, 128.8, 68.5, 51.9, 45.1, 34.2, 25.4, 24.6, 23.0 ppm; IR (CHCl$_3$) 3610, 3480 (broad), 3030, 3010, 1715 (shoulder at ~1730), 1440, 1230 cm$^{-1}$; [α]$_D^{20}$−13.3° (c 0.867 g/dL, CH$_3$Cl$_3$) (+1202° at 365 nM); UV (CH$_3$OH) λ$_{max}$=221 nM; CD [θ]$^{25}$(nM) −11900 (320), +64909 (224) (CH$_3$OH); Anal. calc'd. for C$_{13}$H$_{18}$O$_4$: C, 65.52; H, 7.61; Found: C, 64.78; H, 7.74. HPLC (Chiralcel OD using 93:7 hexane in isopropanol as eluant) indicated that purified acetate (2R) was of 92% ee in R-isomer and that recovered alcohol (1S) was 99.4% ee in S-isomer.

EXAMPLE 14

Mitsunobu Inversion of Methyl 7-(3S-hydroxy-5-oxo-1-cyclopenten-1-yl)-4Z-heptenoate (1S)

To a mixture of 7.14 g (30.0 mmol) of the title alcohol, 15.70 g (60.0 mmol) of triphenylphosphine in THF (100 mL) under argon was added formic acid via syringe. The solution was cooled to ~10° C. in an ice bath. The reaction mixture was maintained at ≦15° C. while 10.44 g (9.49 mL, 60.0 mmol) of diethyl azodicarboxylate was added dropwise via syringe. The pale yellow solution was warmed to room temperature and stirred at room temperature overnight. TLC (80% ethyl acetate/hexane on silica gel) showed complete consumption of starting alcohol. The solvents were removed at reduced pressure to give a viscous oil. This was dissolved in 200 mL of t-butyl methyl ether (TBME) and to this was slowly added 400 mL of hexane and stirred at room temperature for 20 min. The mixture was filtered. The filter pad was washed with two 100-mL portions of 1:1 TBME:hexane. The combined filtrates were concentrated at reduced pressure to give 12.80 g of an amber oil which was dissolved in 300 mL of absolute methanol and stirred mechanically. To this was added gradually 200 g Woelm Super I (neutral) alumina. The mixture was stirred at room temperature for 5 hours to hydrolyze the formate ester intermediate. The mixture was filtered through a glass fritted funnel and the filter cake was washed with three 100-mL portions of CH$_3$OH. The combined filtrates were concentrated at reduced pressure to give ~12 g residue which was purified by flash chromatography on silica gel using gradient elution (30 to 75% ethyl acetate in hexane) to give 8.22 g of product which still contains 6–10% of 1,2-dicarbethoxyhydrazine (determined by $^1$H NMR) which is removed in the subsequent step. An analytical sample was obtained by PTLC on 2000μ silica gel plates using two elutions of 65% ethyl acetate in hexane. The twice purified sample was identical to 3S-alcohol by normal phase HPLC, TLC, $^1$H and $^{13}$C NMR, UV and IR spectroscopy. [α]$_D^{25}$+16.6° (c 1.024 g/dL, CHCl$_3$)(−1174° at 365 nM). CD [θ]$^{25}$ (nM) −11900 (320) (negative maximum), +64909 (224) (positive maximum) (CH$_3$OH). HPLC on Chiralcel OD using 93/7 hexane/isopropanol as eluant indicated that the ratio of 3R to 3S alcohols was 99.4/0.6.

EXAMPLE 15

Preparation of Methyl 7-(3R-hydroxy-5-oxo-1-cyclopenten-1-yl)-4Z-heptenoate (1R) from Methyl 7-[3R-(acetyloxy)-5-oxo-1-cyclopenten-1-yl]-4Z-heptenoate (2R) via deacylation A stock solution of 0.5M guanidine in CH$_3$OH was prepared by adding 1.78 g (77.4 mmol) of 3× hexane washed sodium spheres to an ice-cooled CH$_3$OH (154 mL) under argon atmosphere. When all the sodium had reacted, 14.22 g (79.0 mmol) of guanidine carbonate was added. This was stirred at room temperature for 25 min and the mixture allowed to stand to settle out precipitated salts. In a separate flask was placed 12.8 g (45.6 mmol) of a ~93:7 mixture of R:S acetate in 50 mL of absolute CH$_3$OH under argon. This was cooled to 0° C. in an ice bath and to it was added via syringe 100 mL of 0.5M guanidine in CH$_3$OH prepared above, over ~5 min. This mixture was stirred at ~10° C. for 5 min. TLC (80% ethyl acetate in hexane on silica gel) showed complete consumption of acetate. To the reaction mixture was then added 2.86 mL (3.0 g, 50.0 mmol) of glacial acetic acid to neutralize the guanidine. After stirring for 5 minutes, solvent was removed at reduced pressure to give a thick slurry. The residue was partitioned between 100 mL of water and 100 mL of 1:1 toluene:ethyl acetate. The aqueous layer was further extracted with two 50-mL portions of ethyl acetate. The combined organic layers were washed with two 50-mL portions of water, 50 mL of brine and dried over sodium sulfate. Removal of solvent at reduced pressure gave a deep amber oil which was purified by flash chromatography on silica gel with 50% ethyl acetate in hexane to give 8.06 g of (1R) (77%) after exhaustive removal of solvent. $^1$H and $^{13}$C NMR were identical to previously isolated pure 3S-alcohol (1S). HPLC on Chiralcel OD using 93/7 hexane/isopropanol as eluant indicated a 93:7 R:S mixture of alcohols which showed that no racemization had taken place during deacylation.

EXAMPLE 16

Enzymatic Optical Enrichment of Methyl 7-(3R-hydroxy-5-oxo-1-cyclopenten-1-yl)-4Z-heptenoate (1R)

A mixture of 7.50 g (31.5 mmol) of 93:7 R:S alcohols, 7.50 g (99, 750 units) of porcine pancreatic lipase in 180 mL of distilled vinyl acetate was stirred vigorously at room temperature for 45 hours. HPLC of an aliquot on Chiralcel OD using 93:7 hexane:isopropanol showed excellent conversion of R alcohol (1R) to the corresponding R acetate (2R). In fact, 98% of available R-alcohol had been consumed to give R-acetate with greater than 98.8% ee. The mixture was filtered through diatomaceous earth and the filter cake washed with two 100-mL portions of methylene chloride. The combined filtrates were concentrated under reduced pressure to give 8.90 g of residue which was purified by chromatography on silica with 20% ethyl acetate in hexane as eluant. By this technique, 7.53 g (85%) of 98.8% ee R-acetate (2R) was obtained which was identical to previously isolated R-acetate by $^1$H and $^{13}$C NMR, HPLC and TLC.

EXAMPLE 17

Deacylation of Optically Enriched Methyl 7-(3R-acetyloxy-5-oxo-1-cyclopenten-1-yl)-4Z-heptenoate (2R)

To a room temperature solution of 7.47 g (26.6 mmol) of 98.8% ee 3R-acetate (2R) in 25 mL of absolute methanol under argon was added dropwise via syringe 5.2 mL (2.6 mmol) of stock 0.5M guanidine in methanol prepared above. The reaction was stirred at room temperature for 30 minutes. TLC on silica gel with 80% ethyl acetate in hexane showed complete conversion of acetate to free alcohol. The reaction was quenched by the addition of 314 μL (5.5 mmol) of glacial acetic acid. The solvent was removed at reduced pressure and the residue partitioned between 150 mL of 1:1 toluene/ethyl acetate and 50 mL of water. The aqueous layer was further extracted with 50 mL of ethyl acetate. The combined organic layers were washed with two 25-mL portions of water, 25 mL of brine and dried over sodium sulfate to give 6.25 g of crude residue. This was purified by flash chromatography on silica gel with gradient elution of 50 to 75% ethyl acetate in hexane to give 4.89 g (77%) of R-alcohol (1R). HPLC on Chiralcel OD using 93:7 hexane:isopropanol as eluant indicated a 98.8% ee for the desired product. This product was identical to previously prepared 3R-alcohol by HPLC, $^1$H and $^{13}$C NMR and TLC.

EXAMPLE 18

Preparation of Methyl 7-[5-oxo-3R-[(triethylsilyl)oxy]-1-cyclopenten-1-yl]-4Z-heptenoate (3)

To a 10° C. solution of 34.6 g (0.136 mole) of 94% pure 3R-alcohol (1R), 34.3 g (0.34 mole) of triethylamine, 4.76 g (0.07 mole) of imidazole in 100 mL of DMF under nitrogen, was added dropwise via syringe 24.0 g (26.7 mL, 0.16 mole) of triethylsilylchloride. The mixture was warmed to room temperature for 4 hours. TLC (silica gel with 1:1 ethyl acetate:hexane as eluant) showed complete conversion of alcohol (R$_f$=0.60). The mixture was poured into 300 mL of 1:1 toluene:hexane and this was washed with 300 mL of water followed by three 100-mL portions of water, then 50 mL of brine and dried over sodium sulfate. Removal of solvent at reduced pressure followed by in vacuo treatment at 2×10$^{-2}$ torr at 50° for 2 hours gave 44.76 g crude product which was purified by chromatography on silica gel using a step gradient of 10 to 20% ethyl acetate in hexane. 40.25 g (84%) of purified TES-enone was obtained in this manner. HPLC on Chiralcel OD using 93:7 hexane:isopropanol indicated an enantiomer ratio (R/S) of 99.3:0.7. $^1$H NMR (CDCl$_3$): δ7.04 (m, 1H, C$_2$H), 5.34 (m, 2H, cis olefin), 4.90 (m, 1H, C$_3$H), 3.68 (S, 3H, OCH$_3$), 2.75 (dd, 1H, C$_{4\beta}$H) J=6.0, 18.0 Hz, 2.29 (dd, 1H, C$_{4\alpha}$H) obscured, 2.4–2.2 (m, 8H, CH$_2$), 1.0 (t, 9H, 3CH$_3$) J=8.0 Hz, 0.67 (q, 6H, 3CH$_2$) J=8 Hz; $^{13}$C NMR (CDCl$_3$): δ206.3, 173.7, 157.3, 146.8, 130.3, 129.0, 69.1, 51.9, 45.9, 34.4, 25.4, 24.8, 23.2, 7.1, 5.1 ppm; IR (CHCl$_3$): 3020, 3010, 1735, 1710, 1440, 1355, 1235, 1080 cm$^{-1}$; UV (CH$_3$OH) λ$_{max}$=222 nM; [α]$_D^{20}$ +12.3° (c 0.814 g/dL, CHCl$_3$) (−1018.4° at 365 nM); CD [θ]$^{25}$ (nM) −12166 (315) (negative maximum); +66507 (224) (positive maximum) (CH$_3$OH); Anal. calc'd. for C$_{19}$H$_{32}$O$_4$Si: C, 64.75; H, 9.15; found: C, 64.67; H, 9.20.

EXAMPLE 19

Enzymatic Resolution of Methyl 7-(3-hydroxy-5-oxo-1-cyclopenten-1-yl)-heptanoate via PPL in Vinyl Acetate (7)

A mixture of 240 mg (1.0 mmol) of the title enone, 240 mg (3192 units) of porcine pancreatic lipase in 3 mL of distilled vinyl acetate was sealed and stirred at room temperature for a total of 9 days. Analysis on HPLC using Chiralcel OC at 50° C. using 90:10 hexane:isopropanol as eluant indicated that remaining alcohol was of >99.8% S-isomer. Resolution of the corresponding acetate was not possible under a variety of conditions. The reaction mixture was filtered through a bed of diatomaceous earth and the filter cake rinsed with methylene chloride. The combined filtrates were concentrated at reduced pressure to give 69 mg of crude residue which was purified by PTLC on silica gel (2000μ) using 65% ethyl acetate in hexane as eluant ($R_f$ (ROH)=0.30 and $R_f$ (ROAc)=0.61). In this manner was isolated 130 mg (46%) of methyl 7-(3R-acetyloxy-5-oxo-1-cyclopenten-1-yl)-heptanoate: $^1$H NMR (CDCl3) δ7.10 (m, $C_2$H, 1H), 5.66 (dm, $C_3$H, 1H), 3.68 (s, OCH3, 3H), 2.87 (dd, $C_{4\beta}$H, 1H) J=6, 19.0 Hz, 2.38 (dd, $C_{4\alpha}$H, 1H) J=2.0, 19 Hz, 2.31 (t, $CH_2$, 2H) J=7.5 Hz, 2.21 (bt, 2H) J=7.5 Hz, 2.10 (s, OAc, 3H), 1.62 (m, 2H), 1.35 (m, 4H); $^{13}$C NMR (CDCl3), δ204.5, 173.8, 170.3, 151.4, 149.6, 70.2, 51.2, 41.3, 33.7, 28.7, 28.5, 26.9, 24.5, 24.3, 20.6 ppm; IR (CHCl3) 3020, 3010, 1715 (shoulder at 1735), 1435, 1370, 1240, 1025 cm$^{-1}$; UV (CH3OH) $\lambda_{max}$=221 nM; $[\alpha]_D^{20}$ +47.6° (c 0.871 g/dL, CHCl3) (−649.3° at 365 nM); CD $[\theta]^{25}$ (nM) −7556 (315) (negative maximum), +49533 (224) (positive maximum); Anal. calc'd. for $C_{15}H_{22}O_5$: C, 63.80; H, 7.86; found: C, 63.32; H, 7.91 and then 99 mg (41%) of methyl 7-(3S-hydroxy-5-oxo-1-cyclopenten-1-yl)-heptanoate, mp=60.1° (DSC), whose $^1$H and $^{13}$C NMR, IR, and UV spectra were identical to racemic alcohol. $[\alpha]_D^{20}$ −9.8° (c 1.072 g/dL, CHCl3) (+1216.5° at 365 nM); CD $[\phi]^{25}$ (nM) −7556 (315) (negative maximum), +49533 (224) (positive maximum) (CH3OH); anal. calc'd. for $C_{13}H_{20}O_4$: C, 64.98; H, 8.39; found: C, 64.78; H, 8.52.

EXAMPLE 20

Enzymatic Resolution of Methyl 7-(3-hydroxy-5-oxo-1-cyclopenten-1-yl)-4-heptynoate via PPL in Vinyl Acetate (4)

A mixture of 116 mg (0.49 mmol) of title compound, 116 mg (1543 units) of porcine pancreatic lipase (PPL) in 3 mL of distilled vinyl acetate was sealed and stirred at room temperature for 7 days. Aliquots were removed every 24 hours for HPLC analysis on Chiralcel OC at 50° C. using 90/10 hexane/isopropanol as eluant. After 4 days, HPLC showed that remaining S-alcohol was of 96% ee in S-isomer. The product acetate could not be resolved under these conditions. The crude reaction mixture was filtered through diatomaceous earth and the filter pad was washed with methylene chloride. The combined filtrates were concentrated at reduced pressure to give 128 mg crude residue. Purification by PTLC on 2000μ silica plates ($R_f$(ROAc)=0.55 and $R_f$ (ROH)=0.28) using 65% ethyl acetate/hexane as eluant gave 58 mg (43%) of methyl 7-(3R-acetyloxy-5-oxo-1-cyclopenten-1-yl)-4-heptynoate $^1$H NMR (CDCl3) δ7.25 (m, $C_2$H, 1H), 5.80 (dm, $C_3$H, 1H), 3.70 (s, OCH3, 3H), 2.88 (dd, $C_{4\beta}$H, 1H) J=6.5, 19 Hz, 2.55–2.3 (m, 4$CH_2$+$C_{4\alpha}$H, 9H), 2.10 (S, OAc, 3H); $^{13}$C NMR (CDCl3) δ204.7, 172.4, 170.5, 152.8, 147.8, 79.4, 79.4, 70.4, 41.7, 41.4, 33.7, 24.1, 20.9, 16.8, 14.6 ppm; IR (CHCl3) 3020, 3010, 1735, 1717, 1437, 1370, 1240, 1027 cm$^{-1}$ $[\alpha]_D^{20}$; +41° (c 0.976 g/dL, CHCl3) (−606.4° at 365 nM); CD $[\theta]^{25}$ (nM) −6022 (315) (negative maximum), +4668 (220 nM) (positive maximum) and 51 mg (45%) of methyl 7-(3S-hydroxy-5-oxo-1-cyclopentenyl)-4-heptynoate whose TLC, $^1$H and $^{13}$C NMR, IR were identical to racemic alcohol; $[\alpha]_D^{20}$ −16.7° (c 0.927 g/dL, CHCl3) (+984.4° at 365 nM); CD $[\theta]^{25}$ (nM) +7690 (312), −55275 (225) (CH3OH).

EXAMPLE 21

Enzymatic Resolution of 3-(3-hydroxy-5-oxo-1-cyclopenten-1-yl) propyne via PPL in Vinyl Acetate (5)

A mixture of 166 mg (1.22 mmol) of the title alcohol, 166 mg (2208 units) of porcine pancreatic lipase in 4 mL of distilled vinyl acetate was sealed and stirred at room temperature for a total of 7 days. Aliquots were removed periodically for assay on Chiralcel OA at 50° C. using 96/4 hexane/isopropanol as eluant. After 7 days, HPLC indicated that remaining S-alcohol was of 98% ee and that the product acetate R/S isomers were again unresolved. The reaction mixture was filtered through diatomaceous earth and the filter cake washed with methylene chloride. The combined filtrates were concentrated at reduced pressure to give 205 mg of crude residue which was purified by PTLC on 2000μ silica gel plates using 65% ethyl acetate in hexane as eluant ($R_f$ (ROAc)=0.60 and $R_f$ (ROH)=0.37). In this manner was isolated 76 mg (35%) of 3-(3R-acetyloxy-5-oxo-1-cyclopenten-1-yl)propyne: $^1$H NMR (CDCl3) δ7.44 (q, $C_2$H, 1H) J=2.1 Hz, 5.75 (m, $C_3$H, 1H), 3.13 (q, $CH_2$, 2H) J=2.1 Hz, 2.93 (dd, $C_{4\beta}$H, 1H) J=2.2, 19.0 Hz, 2.21 (t, C≡C—H 1H) J=5.3 Hz, 2.11 (s, OAc, 3H); $^{13}$C NMR (CDCl3) δ202.6, 170.2, 153.5, 144.7, 78.8, 71.2, 69.8, 41.6, 20.7, 15.2 ppm; IR (CHCl3): 3300, 3020, 3010, 1740, 1720, 1640, 1410, 1370, 1240, 1025 cm$^{-1}$; UV (CH3OH) $\lambda_{max}$=219 nM; $[\alpha]_D^{20}$ 52.2° (c 0.928 g/dL, CHCl3) (−713° at 365 nM); CD $[\theta]^{25}$ (nM) −3968 (319), +27494 (216) (CH3OH), no elemental analysis, and 65 mg (48%) of 3-(3S-hydroxy-5-oxo-1-cyclopenten-1-yl)propyne whose $^1$H NMR, IR, and UV were identical to racemic alcohol; $[\alpha]_D^{20}$ −8.7° (c 0.863 g/dL, CHCl3) (+1693° at 365 nM; CD $[\theta]^{25}$ (nM) +9923 (318 nM), −50781 (224) (CH3OH).

EXAMPLE 22

Enzymatic Resolution of Methyl 7-(3-hydroxy-5-oxo-1-cyclopenten-1-yl)-5Z-heptenoate via PPL in Vinyl Acetate (6)

A mixture of 83 mg (0.35 mmol) of the title alcohol, 83 mg (1104 units) of porcine pancreatic lipase in 3.0 mL of distilled vinyl acetate was sealed and stirred at room temperature for a total of 7 days. Aliquots were removed every 24 hours for HPLC analysis on Chiralcel OD using 97/3 hexane/isopropanol as eluant. After 7 days, HPLC indicated that remaining alcohol had a 96/4 S/R in isomer ratio and that this ratio was still improving. Nevertheless, the mixture was filtered through bed of diatomaceous earth and the filter pad was rinsed with methylene chloride. The combined filtrates were concentrated at reduced pressure to give 86 mg crude residue. PTLC on 2000μ silica gel plates using 65% ethyl acetate in hexane as eluant gave 45 mg ($R_f$=0.61, 46%) of methyl 7-(3R-acetyloxy-5-oxo-1-cyclopentene-1-yl)-5Z-heptenoate: $^1$H NMR (CDCl$_3$) δ7.12 (m, C$_2$H, 1H), 5.72 (dm, C$_3$H, 1H), 5.47 (m, olefinic H, 2H), 3.68 (s, OCH$_3$, 3H), 2.96 (m, bis allylic CH$_2$), 2.89 (dd, C$_{4\beta}$H, 1H) J=6.5, 19.0 Hz, 2.48 (dd, C$_{4\alpha}$H, 1H) J=6.5, 19.0 Hz, 2.48 (dd, C$_{4\alpha}$H, 1H) J=2.1, 19.0 Hz, 2.31 (t, CH$_2$CO$_2$, 2H) J=10.1 Hz, 2.10 (m, 2H), 2.10 (s, OAc, 3H), 1.70 (quint, isolated CH$_2$, 2H) J=7.5 Hz; IR (CHCl$_3$) 3020, 3010, 1715 (shoulder at ~1735), 1435, 1370, 1240, 1025 cm$^{-1}$; [α]$_D^{20}$ +47.1° (c 0.935 g/dL, CHCl$_3$) (−649.2° at 365 nM); UV (CH$_3$OH) λ$_{max}$=218 nM; CD [θ]$^{25}$ (nM) −7556 (315), +49533 (224) (CH$_3$OH); anal. calc'd. for C$_{15}$H$_{20}$O$_5$: C, 63.81; H, 7.14; found: C, 63.65; H, 7.04 and then 33 mg ($R_f$=0.34, 40%) of methyl 7-(3S-hydroxy-5-oxo-1-cyclopenten-1-yl)-5Z-heptenoate whose $^1$H NMR, IR, TLC were identical to racemic alcohol; [α]$_D^{20}$ −19.9° (c 0.627 g/dL, CHCl$_3$) (+1031° at 365 nM); CD [θ]$^{25}$ (nM) +24731 (314), −175176 (225) (CH$_3$OH), no elemental analysis.

EXAMPLE 23

Immobilization of PSL Using XAD-8 Resin

A solution of PSL (100 mg) in 10 ml of 0.05M phosphate buffer solution (pH=7.0) was mixed with 10 g of polystyrene beads (XAD-8 from Sigma). The suspension was stirred overnight at 8° C. Most of the water was removed by pipet, the residue was dried over a vacuum pump (rt, 24 hours) to give the immobilized enzyme which was directly used for transesterification.

The foregoing description has been for purposes of illustration. Those skilled in the art will appreciate a number of variations and modifications therefrom. The following claims are intended to cover all modifications and variations within the true spirit and scope of the present invention.

What is claimed is:

1. A method for resolution of a compound of the formula:

wherein X represents alkyl, alkenyl or alkynyl of from 2 to 10 carbon atoms, optionally including a S or O atom at the 2, 3, 4, 5, 6, 7, 8 or 9 position, and R is —CH$_2$OR$_1$ or —CO$_2$R$_2$, wherein R$_1$ is hydrogen, alkyl of 1 to 6 carbon atoms, tetrahydropyranyl, ethoxyethyl, acyl, or (R$_3$)$_3$Si, wherein R$_3$ is independently alkyl of 1-10 carbon atoms or aryl, and wherein R$_2$ is alkyl of 1-6 carbon atoms, said method comprising:
    mixing said compound with a lipase in the presence of an acylating reagent in an organic solvent in the absence of water of thereby obtain the corresponding S alcohol and R acetate; and
    treating said S alcohol with diethylazodicarboxylate, triphenylphospine and formic acid followed by the hydrolysis of the intermediate formate ester with neutral alumina and methanol to obtain the corresponding R alcohol compound with essentially complete inversion.

2. The method claim 1 wherein the acylating reagent is selected from the group consisting of isopropenyl acetate, isopropenyl valerate, vinyl acetate, vinyl propionate and vinyl valerate.

3. The method of claim 2 wherein the lipase is selected from the group consisting of Pseudomonas species lipase, porcine pancreas lipase, *Candida Cylindracea*, *Aspergillus niger* and cholesterol esterase.

4. The method of claim 1 wherein the lipase is porcine pancreas lipase of Pseudomonas species lipase.

5. The method of claim 4 wherein the acylating reagent is isopropenyl acetate or vinyl acetate.

6. The method of claim 1 wherein the lipase is porcine pancreas lipase, the acylating reagent is vinyl acetate and said compound is selected from the group consisting of methyl 7-(3-hydroxy-5-oxo-1-cyclopenten-1-yl)-4Z-heptenoate, methyl 7-(3-hydroxy-5-oxo-1-cyclopenten-1-yl)-4-heptynoate, 3-(3-hydroxy-5-oxo-1-cyclopenten-1-yl)propyne, methyl 7-(3-hydroxy-5-oxo-1-cyclopenten-1-yl)-5Z-heptenoate, and methyl 7-(3-hydroxy-5-oxo-1-cyclopenten-1-yl)heptanoate.

7. The method of claim 6 wherein said compound is methyl 7-(3-hydroxy-5-oxo-1-cyclopenten-1-yl)-4Z-heptenoate.

8. The method of claim 6 wherein the lipase is immobilized on a support.

9. The method of claim 1 wherein the lipase is mixed with the acylating reagent in the presence of a solvent selected from the group consisting of CHCl$_3$, benzene, toluene, t-butylmethyl ether, tetrahydrofuran, diethyl ether or hexane.

10. A method for resolution of a compound of the formula:

wherein X represents alkyl, alkenyl or alkynyl of from 2 to 10 carbon atoms, optionally including a S or O atom at the 2, 3, 4, 5, 6, 7, 8 or 9 position, and R is —CH$_2$OR$_1$ or —CO$_2$R$_2$, wherein R$_1$ is hydrogen, alkyl of 1 to 6 carbon atoms, tetrahydropyranyl, ethoxyethyl or acyl, and wherein R$_2$ is alkyl of 1 to 6 carbon atoms, said method comprising:
    mixing said compound with lipase in the presence of any acylating reagent in an organic solvent in the absence of water to thereby obtain the corresponding S alcohol and R acetate;
    treating said R acetate compound with guanidine and an alcohol to obtain the corresponding R alcohol;
    mixing said R alcohol with a lipase in the presence of an acylating reagent to thereby obtain the corresponding R acetate; and
    treating said R acetate with guanidine and an alcohol to thereby obtain the optically pure R alcohol compound.

11. The method of claim 10 wherein the acylating reagent is selected from the group consisting of isopropenyl acetate, isopropenyl valerate, vinyl acetate, vinyl propionate and vinyl valerate.

12. The method of claim 11 wherein the lipase is selected from the group consisting of Pseudomonas species lipase, porcine pancreas lipase and *Candida cylindracea* lipase.

13. The method of claim 10 wherein the lipase is porcine pancreas lipase or *Pseudomonas* species lipase.

14. The method of claim 13 wherein the acylating reagent is isopropenyl acetate or vinyl acetate.

15. The method of claim 1 wherein the lipase is porcine pancreas lipase, the acylating reagent is vinyl acetate and said compound is selected from the group consisting of methyl 7-(3-hydroxy-5-oxo-1-cyclopenten-1-yl)-4-heptenoate, methyl 7-(3-hydroxy-5-oxo-1-cyclopenten-1-yl)-4-heptynoate, 3-(3-hydroxy-5-oxo-1-cyclopenten-1-yl)propyne, methyl 7-(3-hydroxy-5-oxo-1-cylopenten-1-yl)-5Z-heptenoate, and methyl 7-(3-hydroxy-5-oxo-1-cyclopenten-1-yl)heptanoate.

16. The method of claim 15 wherein said compound is methyl 7-(3-hydroxy-5-oxo-1-cyclopenten-1-yl)-4Z-heptenoate.

17. The method of claim 13 wherein the lipase is immobilized on a support.

18. The method of claim 10 wherein the lipase is mixed with the acylating reagent in the presence of a solvent selected from the group consisting of $CHCl_3$, benzene, toluene, t-butylmethyl ether, tetrahydrofuran, diethyl ether or hexane.

* * * * *

UNITED STATES PATENT AND TRADEMARK OFFICE
CERTIFICATE OF CORRECTION

PATENT NO. : 5,106,750

DATED : April 21, 1992

INVENTOR(S) : Wong, et al.

It is certified that error appears in the above-identified patent and that said Letters Patent is hereby corrected as shown below:

Column 2, line 42, reading "90°C" should read -- 94°C --.

Column 3, line 7, reading "disapperance" should read -- disappearance --.

Column 7, line 28, reading "Pseudomonas" should read -- *Pseudomonas* --.

Column 7, line 37, reading "-camphorato]europuim" should read -- camphorato)europium --.

Column 7, line 56, reading "monacetate" should read -- monoacetate --.

Column 7, line 60, reading "catayzed" should read -- catalyzed --.

Col. 14, line 60. "Table 5, 3rd Structure, reading "19a R=H 19b R=Ac" should read --20a R=H 20b R=Ac--

Column 16, line 45, reading "Cß)," should read -- (Cß), --.

Column 18, line 51, reading "CH$_2$OR$_1$" should read -- -CH$_2$OR$_1$ --.

Column 18, line 53, reading "ethoxyethyl," should read -- ethoxyethyl --.

Column 24, line 33, reading "$\leqq$ 15°C" should read -- $\leq$15°C --.

Column 29, line 59, reading "water of" should read -- water to --.

UNITED STATES PATENT AND TRADEMARK OFFICE
CERTIFICATE OF CORRECTION

PATENT NO.   : 5,106,750

DATED        : April 21, 1992

INVENTOR(S)  : Wong, et al.

It is certified that error appears in the above-identified patent and that said Letters Patent is hereby corrected as shown below:

Column 30, line 49, reading "with lipase" should read -- with a lipase --.

Signed and Sealed this

Twelfth Day of April, 1994

BRUCE LEHMAN

*Attest:*

*Attesting Officer*

*Commissioner of Patents and Trademarks*